United States Patent
Luedtke et al.

(10) Patent No.: US 6,890,938 B2
(45) Date of Patent: May 10, 2005

(54) INDOLE-TYPE INHIBITORS OF P38 KINASE

(75) Inventors: Gregory Luedtke, Sunnyvale, CA (US); Richland Tester, San Jose, CA (US); Sundeep Dugar, San Jose, CA (US); Qing Lu, Foster City, CA (US); John Perumattam, Los Altos, CA (US); Xuefei Tan, Sunnyvale, CA (US)

(73) Assignee: Scios, Inc., Fremont, CA (US)

( * ) Notice: Subject to any disclaimer, the term of this patent is extended or adjusted under 35 U.S.C. 154(b) by 0 days.

(21) Appl. No.: 09/989,991

(22) Filed: Nov. 20, 2001

(65) Prior Publication Data

US 2003/0100588 A1 May 29, 2003

Related U.S. Application Data

(60) Provisional application No. 60/252,163, filed on Nov. 20, 2000.

(51) Int. Cl.[7] ..................... A61K 31/445; C07D 401/06
(52) U.S. Cl. ..................... 514/323; 514/409; 546/201; 548/409
(58) Field of Search ................... 514/323, 409; 546/201; 548/409

(56) References Cited

U.S. PATENT DOCUMENTS

| | | | |
|---|---|---|---|
| 5,166,136 A | * | 11/1992 | Ward et al. .................. 514/15 |
| 2002/0160388 A1 | * | 10/2002 | Macina et al. ................ 435/6 |
| 2003/0109682 A1 | * | 6/2003 | Santi et al. ............... 530/391.1 |

FOREIGN PATENT DOCUMENTS

| | | |
|---|---|---|
| WO | WO 96/4043 | 12/1996 |
| WO | WO 97/26252 | 7/1997 |
| WO | WO 98/06715 | 2/1998 |
| WO | WO 98/07425 | 2/1998 |
| WO | WO 99/61426 | 12/1999 |
| WO | WO 00/12074 | 3/2000 |
| WO | WO 00/59904 | 10/2000 |
| WO | WO 00/71535 | 11/2000 |
| WO | WO 01/64676 | 9/2001 |

OTHER PUBLICATIONS

Cohen et al. "Cytokine function: a study in biologic diversity" CA 125:31527 (1996).*
Kon et al. "Preparation of diazepine–substituted . . . " CA 118:169124 (1993).*
Hall et al. "Preparation of balanoids as . . . " CA 123:198645 (1995).*
Biller et al. "Preparation of heterocyclic inhibitors . . . " CA 128:282780 (1998).*
Brana et al. "Chemoselective michael reactions . . . " CA 137:279446 (2002).*
CRC Handbook of chemistry and physics, p. 9–40, (2002).*
Rubini et al. "Synthesis of isoteric methylene–oxy . . . " Tetrahedron v.42, p. 6039–6045 (1986).*

* cited by examiner

*Primary Examiner*—Celia Chang
(74) *Attorney, Agent, or Firm*—Morrison & Foerster LLP

(57) ABSTRACT

Compound with an indole linked through an aliphatic ring system to an aromatic moiety are useful in treating conditions associated with enhanced P38α kinase activity.

28 Claims, No Drawings

INDOLE-TYPE INHIBITORS OF P38 KINASE

CROSS-REFERENCE TO RELATED APPLICATIONS

This application claims priority under 35 U.S.C. §119(e) from U.S. Ser. No. 60/252,163 filed 20 Nov. 2000.

FIELD OF THE INVENTION

The invention relates to treating various disorders associated with enhanced activity of kinase p38-β. More specifically, it concerns indole-type derivatives useful in these methods.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

Eye diseases associated with a fibroproliferative condition include retinal reattachment surgery accompanying proliferative vitreoretinopathy, cataract extraction with intraocular lens implantation, and post glaucoma drainage surgery.

PCT applications WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

Certain aroyl/phenyl-substituted piperazines and piperidines which inhibit p38-α kinase are described in PCT publication WO00/12074 published 9 Mar. 2000. In addition, indolyl substituted piperidines and piperazines which inhibit this enzyme are described in PCT publication No. WO99/61426 published 2 Dec. 1999. Carbolene derivatives of piperidine and piperazine as p38-α inhibitors are described in PCT/US00/07934 filed 24 Mar. 2000.

None of the foregoing patents describes the indole derivatives described herein which specifically inhibit p38-α.

SUMMARY OF THE INVENTION

The invention is directed to methods and compounds useful in treating conditions that are characterized by enhanced p38-α activity. These conditions include inflammation, proliferative diseases, and certain cardiovascular disorders as well as Alzheimer's disease as further described below.

Compounds of the invention inhibit p38 kinase, the α-isoform in particular, and are thus useful in treating diseases mediated by these activities. The compounds of the invention are of the formula

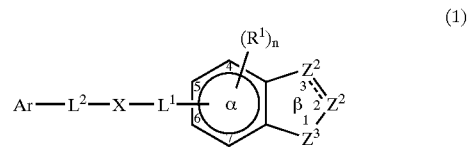

(1)

and the pharmaceutically acceptable salts thereof, or a pharmaceutical composition thereof, wherein:

Ar is an aryl group substituted with 0–5 non-interfering substituents, wherein two adjacent noninterfering substituents can form a fused aromatic or nonaromatic ring;

$L^1$ and $L^2$ are linkers;

X is an aliphatic monocyclic or aliphatic polycyclic moiety optionally comprising one or more hetero ring atoms wherein the cyclic moiety may be optionally substituted with one or more noninterfering substituents and where said optional substituents may constitute a ring fused to X;

n is 0–3;

each $R^1$ is hydrogen or a noninterfering substituent;

represents a single or double bond;

one $Z^2$ is CA or $CR^2A$; the other $Z^2$ is $CR^3$, $CR^3{}_2$, $NR^4$ or N; and each $R^2$, $R^3$ and $R^4$ is independently hydrogen or a noninterfering substituent;

$Z^3$ is $NR^5$ or O; where $R^5$ is hydrogen or a noninterfering substituent;

A is $-W_i-COX_jY$, where Y is $COR^6$ or an isostere thereof, each of W and X is a spacer of 2–6 Å; each of i and j is independently 0 or 1; and $R^6$ is a noninterfering substituent;

and wherein the smallest number of covalent bonds in the compound separating the atom of Ar linked to $L^2$ and the atom of the α ring linked to $L^1$ is at least 5, each said bond having a bond length of 1.2 to 2.0 angstroms; and/or the distance in space between the atom of Ar linked to $L^2$ and the atom of the α ring linked to $L^1$ is 4.5–24 angstroms.

and with the proviso that the portion of the compound represented by $L^2$-X-$L^1$ is not:

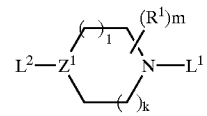

where $L^2$ and $L^1$ are linkers; $Z^1$ is CR or N wherein R is hydrogen or a non-interfering substituent; each $R^1$ is independently a non-interfering substituent; and each of l and k is 0–3; and m is 0–4.

The invention is further directed to methods of treating inflammation or proliferative conditions using these compounds. The invention is also directed to treating conditions associated with cardiac failure and Alzheimer's disease using the invention compounds.

DETAILED DESCRIPTION

The compounds of formula (1) are useful in treating conditions which are characterized by overactivity of p38 kinase, in particular the α-isoform. Conditions "characterized by enhanced p38-α activity" include those where this enzyme is present in increased amount or wherein the enzyme has been modified to increase its inherent activity, or both. Thus, "enhanced activity" refers to any condition wherein the effectiveness of these proteins is undesirably high, regardless of the cause.

The compounds of the invention are useful in conditions where p38-α kinase shows enhanced activity. These conditions are those in which fibrosis and organ sclerosis are caused by, or accompanied by, inflammation, oxidation injury, hypoxia, altered temperature or extracellular osmolarity, conditions causing cellular stress, apoptosis or necrosis. These conditions include ischemia-reperfusion injury, congestive heart failure, progressive pulmonary and bronchial fibrosis, hepatitis, arthritis, inflammatory bowel disease, glomerular sclerosis, interstitial renal fibrosis, chronic scarring diseases of the eyes, bladder and reproductive tract, bone marrow dysplasia, chronic infectious or autoimmune states, spinal chord injury and traumatic or surgical wounds. These conditions, of course, would be benefited by compounds which inhibit p38-α. Methods of treatment with the compounds of the invention are further discussed below.

The compounds useful in the invention are derivatives of indole-type compounds containing a mandatory substituent, A, at a position corresponding to the 2- or 3-position of indole. In general, an indole-type nucleus is preferred, although alternatives within the scope of the invention are also illustrated below.

In the description above, certain positions of the molecule are described as permitting "noninterfering substituents." This terminology is used because the substituents in these positions generally speaking are not relevant to the essential activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound of formula (1) to inhibit p38-α activity qualitatively intact. Thus, the substituent may alter the degree of inhibition of p38-α. However, as long as the compound of formula (1) retains the ability to inhibit p38-α activity, the substituent will be classified as "noninterfering." A number of assays for determining the ability of any compound to inhibit p38-α activity are available in the art. A whole blood assay for this evaluation is illustrated below. The gene for p38-α has been cloned and the protein can be prepared recombinantly and its activity assessed, including an assessment of the ability of an arbitrarily chosen compound to interfere with this activity. The essential features of the molecule are tightly defined. The positions which are occupied by "noninterfering substituents" can be substituted by conventional organic moieties as is understood in the art. It is irrelevant to the present invention to test the outer limits of such substitutions. The essential features of the compounds are those set forth with particularity herein.

In addition, $L^1$ and $L^2$ are described herein as linkers. The nature of such linkers is less important than the distance they impart between the portions of the molecule. Typical linkers include alkylene, i.e. $(CH_2)_n$—R; alkenylene—i.e., an alkylene moiety which contains a double bond, including a double bond at one terminus. Other suitable linkers include, for example, substituted alkylenes or alkenylenes, carbonyl moieties, and the like.

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when so stated however, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue.

As used herein, "inorganic residue" refers to a residue that does not contain carbon. Examples include, but are not limited to, halo, hydroxy, $NO_2$ or $NH_2$.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Heteroalkyl, heteroalkenyl and heteroalkynyl are similarly defined but may contain 1–2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5–12 ring member atoms.

Similarly, "arylalkyl" and "heteroalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide substituents as an acyl moiety.

When the compounds of Formula 1 contain one or more chiral centers, the invention includes optically pure forms as well as mixtures of stereoisomers or enantiomers.

With respect to the portion of the compound between the Ar and the ring α, linkers $L^2$ and $L^1$, in combination with the moiety —X—, provide for separation of the atom of Ar bonded to $L^2$ from the atom of the ring α bonded to $L^1$ by a defined minimum number of covalent bond distances counted end-to-end through the compound, as opposed to a measurement of linear distance through space. More particularly, the smallest number of bonds counted end-to-end in the compound separating the atom of Ar bonded to $L^2$ from the atom of the ring α bonded to $L^1$ is at least 5, and preferably from 6 to 12, wherein the length of each of such bonds is 1.2 to 2.0 angstroms. In terms of a linear distance through space, the linear distance measured through space from the atom of Ar bonded to $L^2$ to the atom of the ring α bonded to $L^1$ is a distance of 4.5–24 Å, preferably 6–20 Å, and more preferably 7.5–10 Å.

Typical, but nonlimiting, embodiments of $L^1$ and $L^2$ are CO and isosteres thereof, or optionally substituted isosteres, or longer chain forms. $L^2$, in particular, may be alkylene or alkenylene optionally substituted with noninterfering substituents or $L^1$ or $L^2$ may be or may include a heteroatom such as N, S or O. Such substituents include, but are limited to, a moiety selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two substituents on $L^2$ can be joined to form a non-aromatic saturated or unsaturated ring that includes 0–3 heteroatoms which are O, S and/or N and which contains 3 to 8 members or said two substituents can be joined to form a carbonyl moiety or an oxime, oximeether, oximeester or ketal of said carbonyl moiety. Further examples of $L^1$ and $L^2$ include —$CH_2$—NH—CO— and —$CH_2$—NH—CO—.

Isosteres of CO and $CH_2$, include SO, $SO_2$, or CHOH. CO and $CH_2$ are preferred.

Thus, $L^2$ is substituted with 0–2 substituents. Where appropriate, two optional substituents on $L^2$ can be joined to form a non-aromatic saturated or unsaturated hydrocarbyl ring that includes 0–3 heteroatoms such as O, S and/or N and which contains 3 to 8 members. Two optional substituents on $L^2$ can be joined to form a carbonyl moiety which can be subsequently converted to an oxime, an oximeether, an oximeester, or a ketal.

Ar is aryl, heteroaryl, including 6-5 fused heteroaryl, cycloaliphatic or cycloheteroaliphatic that can be optionally substituted. Ar is preferably optionally substituted phenyl.

Each substituent on Ar is independently a hydrocarbyl residue (1-20C) containing 0–5 heteroatoms selected from O, S and N, or is an inorganic residue. Preferred substituents include those selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two of said optional substituents on adjacent positions can be joined to form a fused, optionally substituted aromatic or nonaromatic, saturated or unsaturated ring which contains 3–8 members. More preferred substituents include halo, alkyl (1-4C) and more preferably, fluoro, chloro and methyl. These substituents may occupy all available positions of the aryl ring of Ar, preferably 1–2 positions, most preferably one position. These substituents may be optionally substituted with substituents similar to those listed. Of course some substituents, such as halo, are not further substituted, as known to one skilled in the art.

Two adjacent substituents on Ar can be joined to form a fused, optionally substituted aromatic or nonaromatic, saturated or unsaturated ring which contains 3–8 members.

Moiety —X— in the compound of formula (I) is an aliphatic monocyclic or aliphatic polycyclic moiety optionally comprising one or more hetero ring atoms wherein the cyclic moiety may be optionally substituted with one or more noninterfering substituents and where said optional substituents may constitute a ring fused to X. Moiety —X— includes bridged cyclic moieties. Examples of cyclic moieties that may serve as moiety X include:

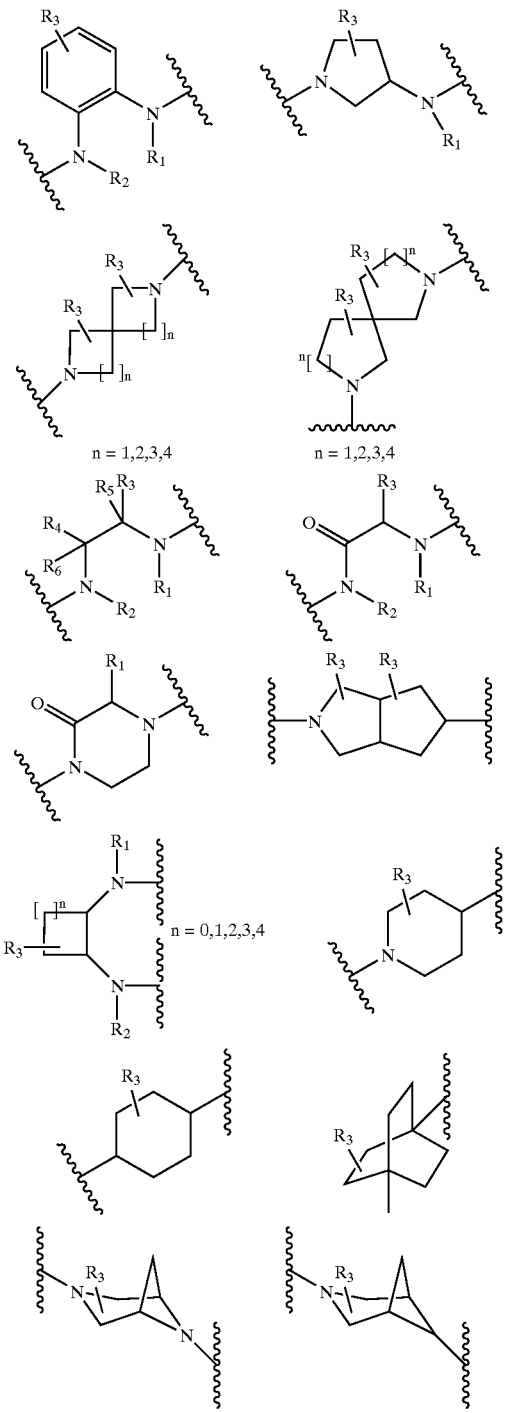

-continued

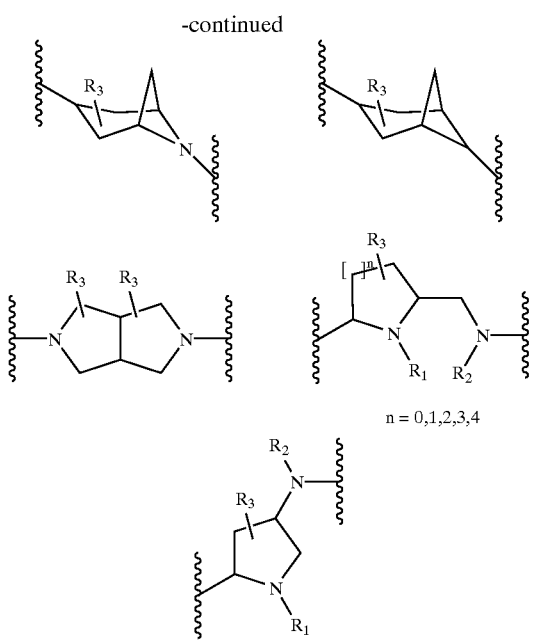

n = 0,1,2,3,4

Particular examples of —X— in compound (I) are cyclic moieties such that the portion of the compound represented by $L^2$-X-$L^1$ is selected from the group consisting of:

 (I)

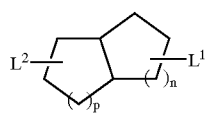 (II)

wherein n and p are independently 0–4 and the sum of n and p is 1 to 6;

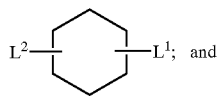 (III)

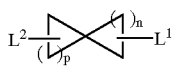 (IV)

wherein n and p are independently 1–4.
wherein, in each of structures (I) to (IV):
one or more of the ring carbon atoms not bound to $L^2$ or $L^1$ may be optionally replaced with $NR^1$, where $R^1$ is hydrogen or a noninterfering substituent; or by $CHR^2$ or $CR^2{}_2$, where $R^2$ is a noninterfering substituent other than hydrogen; and
one or both of the ring carbon atoms bound to $L^2$ and $L^1$ may be independently replaced with $CR^3$ or N where $R^3$ is independently a noninterfering substituent other than hydrogen.

The noninterfering substituents $R^5$ (i.e. when $Z^3$ is $NR^5$) include, without limitation, halo, alkyl, alkoxy, aryl, arylalkyl, aryloxy, heteroaryl, acyl, carboxy, or hydroxy. Preferably, $R^5$ is H, alkyl, OR, $NR_2$, SR or halo, where R is H or alkyl. Additionally, $R^5$ can be joined with an $R^1$ substituent (defined below) to form an optionally substituted non-aromatic saturated or unsaturated hydrocarbyl ring which contains 3–8 members and 0–3 heteroatoms such as O, N and/or S. Preferred embodiments include compounds wherein $Z^1$ is CH or N, and those wherein both l and k are 1.

Substituents $R^2$ and $R^3$ optionally bonded to the moiety —X— represent independently a noninterfering substituent such as a hydrocarbyl residue (1-20C) containing 0–5 heteroatoms selected from O, S and N. Preferably $R^2$ and $R^3$ are independently alkyl, alkoxy, aryl, arylalkyl, aryloxy, heteroalkyl, heteroaryl, heteroarylalkyl, RCO, =O, acyl, halo, CN, OR, NRCOR, NR, wherein R is H, alkyl (preferably 1-4C), aryl, or hetero forms thereof. Each appropriate substituent is itself unsubstituted or substituted with 1–3 substituents. The substituents are preferably independently selected from a group that includes alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and two of $R^2$ and/or $R^3$ on adjacent positions can be joined to form a fused, optionally substituted aromatic or nonaromatic, saturated or unsaturated ring which contains 3–8 members, or $R^2$ and $R^3$ independently are =O or an oxime, oximeether, oximeester or ketal thereof. Preferred embodiments of $R^2$ and $R^3$ comprise alkyl (1-4C) especially two alkyl substituents and carbonyl. Most preferably $R^2$ and $R^3$ comprise methyl groups or carbonyl groups. The —X— moiety may be chiral, hence an isolated enantiomer may be preferred.

$R^1$ represents a noninterfering substituent. Such substituents include hydrocarbyl residues (1-6C) containing 0–2 heteroatoms selected from O, S and/or N and inorganic residues. n is an integer of 0–3, preferably 0 or 1. Preferably, the substituents represented by $R^1$ are independently halo, alkyl, heteroalkyl, OCOR, OR, NRCOR, SR, or $NR_2$, wherein R is H, alkyl, aryl, or heteroforms thereof. More preferably $R^1$ substituents are selected from alkyl, alkoxy or halo, and most preferably methoxy, methyl, and chloro. Most preferably, n is 0 and the α ring is unsubstituted, except for $L^1$ or n is 1 and $R^3$ is halo or methoxy.

In the ring labeled β, $Z^3$ may be $NR^5$ or O—i.e., the compounds may be related to indole or benzofuran. If $C^3$ is $NR^5$, preferred embodiments of $R^5$ include H or optionally substituted alkyl, alkenyl, alkynyl, aryl, arylalkyl, acyl, aroyl, heteroaryl, heteroalkyl, heteroalkenyl, heteroalkynyl, heteroalkylaryl, or is SOR, $SO_2R$, RCO, COOR, alkyl-COR, $SO_3R$, $CONR_2$, $SO_2NR_2$, CN, $CF_3$, $NR_2$, OR, alkyl-SR, alkyl-SOR, alkyl-$SO_2R$, alkyl-OCOR, alkyl-COOR, alkyl-CN, alkyl-$CONR_2$, or $R_3Si$, wherein each R is independently H, alkyl, alkenyl or aryl or heteroforms thereof. More preferably, $R^5$ is hydrogen or is alkyl (1-4C), preferably methyl or is acyl (1-4C), or is COOR wherein R is H, alkyl, alkenyl of aryl or hetero forms thereof. $R^5$ is also preferably a substituted alkyl wherein the preferred substituents are form ether linkages or contain sulfinic or sulfonic acid moieties. Other preferred substituents include sulfhydryl substituted alkyl substituents. Still other preferred substituents include $CONR_2$ wherein R is defined as above.

It is preferred that the indicated dotted line represents a double bond; however, compounds which contain a saturated β ring are also included within the scope of the invention.

Preferably, the mandatory substituent CA or $CR^2A$ is in the 3-position; however, regardless of which position this substituent occupies, the other position is $CR^3$, $CR^3{}_2$, $NR^4$ or N. $CR^3$ is preferred. Preferred embodiments of $R^3$ include hydrogen, alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and two of $R^3$ can be joined to form a fused, optionally substituted aromatic or nonaromatic, saturated or unsaturated ring which contains 3–8 members. Most preferably, $R^3$ is H, alkyl, such as methyl, most preferably, the ring labeled β contains a double bond and $CR^3$ is CH or C-alkyl. Other preferable forms of $R^3$ include H, alkyl, acyl, aryl, arylalkyl, heteroalkyl, heteroaryl, halo, OR, $NR_2$, SR, NRCOR, alkyl-OOR, RCO, COOR, and CN, wherein each R is independently H, alkyl, or aryl or heteroforms thereof.

While the position not occupied by CA is preferred to include $CR^3$, the position can also be N or $NR^4$. While $NR^4$ is less preferred (as in that case the ring labeled β would be saturated), if $NR^4$ is present, preferred embodiments of $R^4$ include H, or alkyl, alkenyl, alkynyl, aryl, arylalkyl, acyl, aroyl, heteroaryl, heteroalkyl, heteroalkenyl, heteroalkynyl, heteroalkylaryl, or is SOR, $SO_2R$, RCO, COOR, alkyl-COR, $SO_3R$, $CONR_2$, $SO_2NR_2$, CN, $CF_3$, or $R_3Si$ wherein each R is independently H, alkyl, alkenyl or aryl or heteroforms thereof.

Preferably, $CR^2A$ or CA occupy position 3- and preferably $Z^2$ in that position is CA. However, if the β ring is saturated and $R^2$ is present, preferred embodiments for $R^2$ include H, halo, alkyl, alkenyl and the like. Preferably $R^2$ is a relatively small substituent corresponding, for example, to H or lower alkyl 1-4C.

A is $—W_i—COX_jY$ wherein Y is $COR^6$ or an isostere thereof and $R^6$ is a noninterfering substituent. Each of W and X is a spacer and may be, for example, optionally substituted alkyl, alkenyl, or alkynyl, each of i and j is 0 or 1. Preferably, W and X are unsubstituted. Preferably, j is 0 so that the two carbonyl groups are adjacent to each other. Preferably, also, i is 0 so that the proximal CO is adjacent the ring. However, compounds wherein the proximal CO is spaced from the ring can readily be prepared by selective reduction of an initially glyoxal substituted β ring. In the most preferred embodiments of the invention, the α/β ring system is an indole containing CA in position 3- and wherein A is $COCR^6$.

The noninterfering substituent represented by $R^6$, when $R^6$ is other than H, is a hydrocarbyl residue (1-20C) containing 0–5 heteroatoms selected from O, S and/or N or is an inorganic residue. Preferred are embodiments wherein $R^6$ is H, or is straight or branched chain alkyl, alkenyl, alkynyl, aryl, arylalkyl, heteroalkyl, heteroaryl, or heteroarylalkyl, each optionally substituted with halo, alkyl, heteroalkyl, SR, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl or aryl or the heteroatom-containing forms thereof, or wherein $R^6$, is OR, $NR_2$, SR, $NRCONR_2$, $OCONR_2$, or $NRSO_2NR_2$, wherein each R is independently H, alkyl, alkenyl or aryl or the heteroatom-containing forms thereof, and wherein two R attached to the same atom may form a 3–8 member ring and wherein said ring may further be substituted by alkyl, alkenyl, alkynyl, aryl, arylalkyl, heteroalkyl, heteroaryl, heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl or aryl or the heteroatom-containing forms thereof wherein two R attached to the same atom may form a 3–8 member ring, optionally substituted as above defined.

Other preferred embodiments of $R^6$ are H, heteroarylalkyl, $—NR_2$, heteroaryl, $—COOR$, $—NHRNR_2$, heteroaryl-COOR, heteroaryloxy, $—OR$, heteroaryl-$NR_2$, $—NROR$ and alkyl. Most preferably $R^6$ is isopropyl piperazinyl, methyl piperazinyl, dimethylamine, piperazinyl, isobutyl carboxylate, oxycarbonylethyl, morpholinyl, aminoethyldimethylamine, isobutyl carboxylate piperazinyl, oxypiperazinyl, ethylcarboxylate piperazinyl, methoxy, ethoxy, hydroxy, methyl, amine, aminoethyl pyrrolidinyl, aminopropanediol, piperidinyl, pyrrolidinyl-piperidinyl, or methyl piperidinyl.

Isosteres of $COR^6$ as represented by Y are defined as follows.

The isosteres have varying lipophilicity and may contribute to enhanced metabolic stability. Thus, Y, as shown, may be replaced by the isosteres in Table 1.

TABLE 1

Acid Isosteres

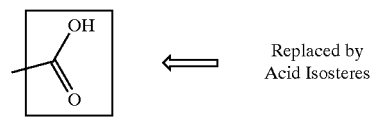

Replaced by Acid Isosteres

| Names of Groups | Chemical Structures | Substitution Groups (SG) |
|---|---|---|
| tetrazole | 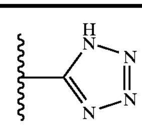 | n/a |
| 1,2,3-triazole | 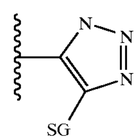 | H; $SCH_3$; $COCH_3$; Br; $SOCH_3$; $SO_2CH_3$; $NO_2$; $CF_3$; CN; COOMe |
| 1,2,4-triazole | 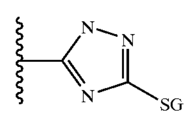 | H; $SCH_3$; $COCH_3$; Br; $SOCH_3$; $SO_2CH_3$; $NO_2$ |
| imidazole | 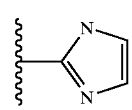 | H; $SCH_3$; $COCH_3$; Br; $SOCH_3$; $SO_2CH_3$; $NO_2$ |

Thus, isosteres include tetrazole, 1,2,3-triazole, 1,2,4-triazole and imidazole.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

Synthesis of the Invention Compounds

Copending, commonly-assigned U.S. Ser. No. 09/575,060, incorporated herein by reference in its entirety, illustrated the following reaction scheme for conversion of a 4-benzyl piperidinyl-indole-5-carboxamide to the glyoxalic acid compounds of the invention and derivatives thereof:

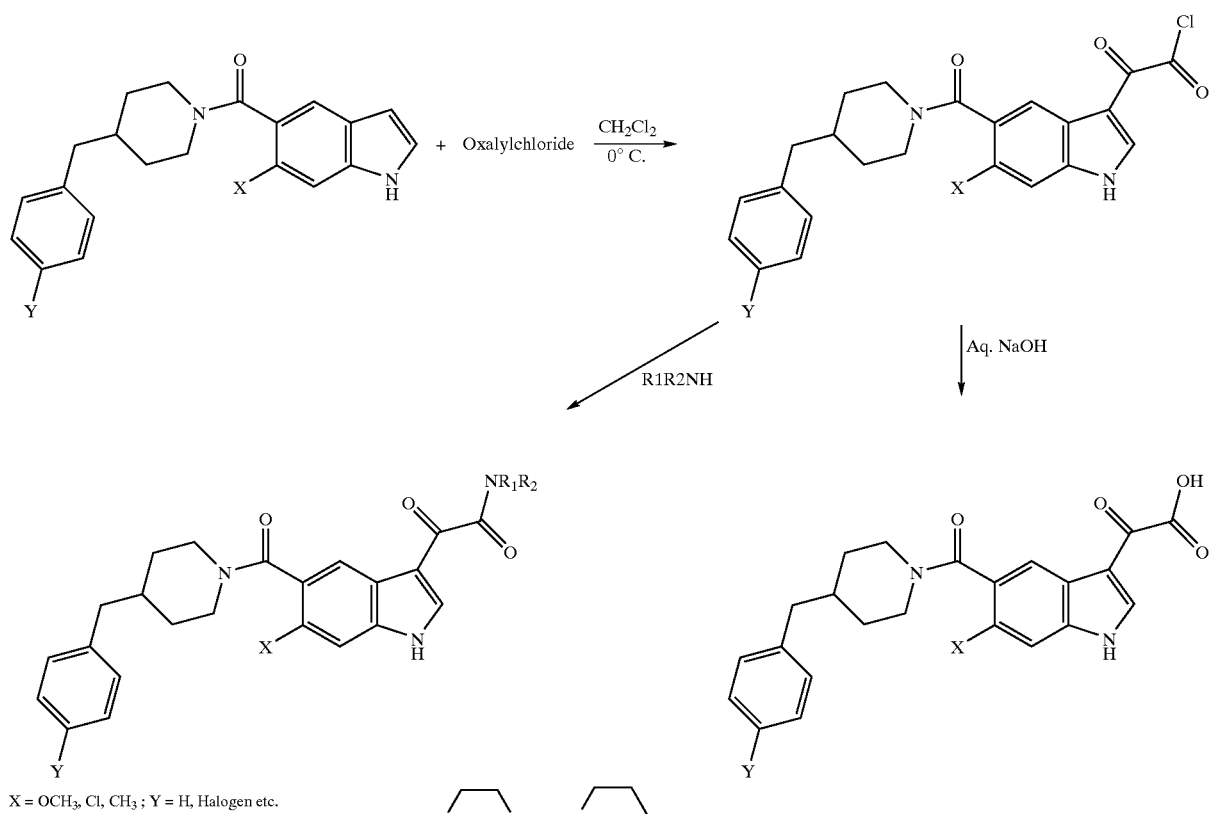

In the present invention, the piperadinyl moiety is generalized to X in formula (I) above where X is an aliphatic monocyclic or aliphatic polycyclic moiety optionally comprising one or more hetero ring atoms wherein the cyclic moiety may be optionally substituted with one or more noninterfering substituents and where said optional substituents may constitute a ring fused to X.

As disclosed commonly assigned in U.S. Ser. No. 09/575,060, the glyoxal type substituent at position 3 can be generalized to $W_iCOX_jY$.

The indole-type moiety may be generalized as:

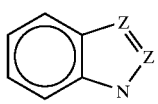

Methods to synthesize the compounds of the invention are, in general, known in the art. The following general schemes illustrate such methods.

Scheme 1

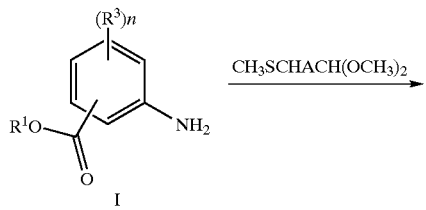

Substituted amino benzoic acid esters such as I can be treated with reagents such as thiomethylacetylaldehyde dimethyl acetal and N-chlorosuccinamide in methylene chloride at low temperature followed by the treatment with a base such as triethylamine at reflux in methylene chloride, dichloroethane or chloroform to give indoles II, Scheme 1. Treatment with reagents such as Raney-Nickel in an appropriate solvent such as ethanol, methanol or isopropanol will yield the corresponding indole carboxylic acid ester which when hydrolyzed under base conditions will give the desired substituted indole carboxylic acid.

Scheme 2

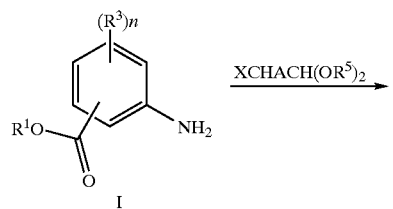

Alternatively, substituted amino benzoic acid esters I can be converted to the ketals IV, Scheme 2, with an appropriate aldehyde under conditions of reductive alkylation with reagents such as sodium triacetoxyborohydride in acetic acid in the presence of sodium sulfate. The amines can then be treated with Lewis acids such as aluminum chloride, titanium chloride, $BF_3$-etherate in dichloromethane or dichloroethane, under reflux to give the corresponding substituted indole methyl esters, with appropriate substitutions.

Scheme 3

Another method could involve the treatment of the substituted amino benzoic acid esters I with iodine and sodium periodate in an appropriate solvent such as dimethylformamide, to give the corresponding iodo aniline V, Scheme 3. This can be coupled with an acetylene such as trimethyl silyl acetylene or ethylethenyl ether in the presence of an appropriate catalysts such as palladium and copper and a base such as triethylamine to give the silyl coupled product such as VI. Subsequent cyclization in a solvent such as dimethylformamide and in the presence of a catalyst such as copper iodide would give the appropriately substituted indoles VII.

Scheme 4

Commonly assigned U.S. Ser. No. 09/575,060 disclosed that piperidine moieties can be obtained by treating an appropriate piperidone such as VIII, Scheme 4, with substituted benzyl phosphonate esters in the presence of a base such as sodium hydride to give alkenes which can be reduced to the corresponding substituted 4-benzylpiperidine such as IX. The hydrogenations are typically done in the presence of catalytic metals in solvents such as methanol, ethanol and ethyl acetate. In the present invention the piperidone VIII could be replaced in the above reaction scheme in a known manner with suitable cyclic moieties correspondingly generally to X as defined in the above formula (1) such that instead of the 4-benzylpiperidone of formula IX, a moiety is obtained having the generalized structure

Scheme 5

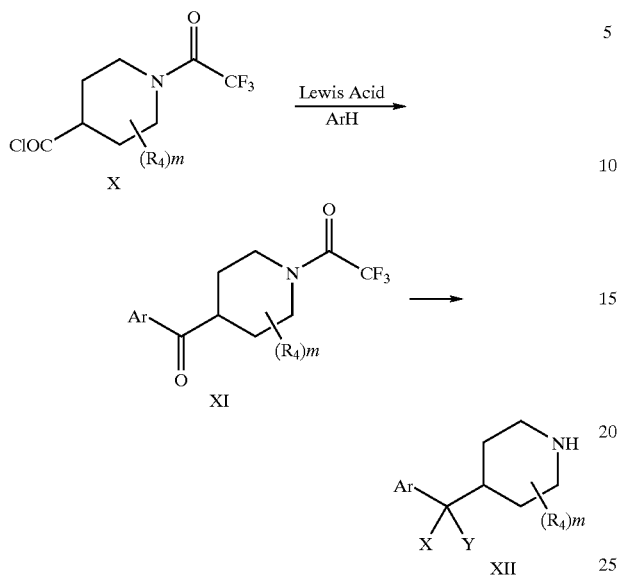

An alternate method disclosed in Commonly assigned U.S. Ser. No. 09/575,060 could involve isonipecotoyl chlorides such as X which can be used to acylate appropriately substituted benzenes (ArH) in the presence of a Lewis acid such as aluminum chloride to give the ketones XI, Scheme 5. Further modifications of the carbonyl moiety of XI using methods and routes generally known can then lead to the desired compounds XII. In the present invention the cyclic precursor in compound X above can be replaced with cyclic moieties corresponding generally to the monocyclic or polycyclic aliphatic moieties defined as "X" in the above formula (1).

Scheme 6

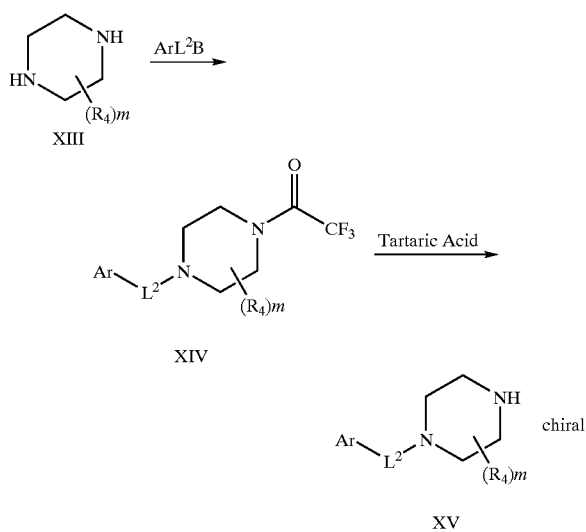

Moreover, in the same manner that substituted piperazines XIII can be reacted with various and appropriate $ArL^2X$ in the presence or absence of a base or other catalytic reagent to give the substituted piperazines XV, Scheme 6, as described in commonly assigned U.S. Ser. No. 09/575,060; compounds comprising the moiety "X" in formula (1) above can also be reacted with $ArL^2X$ in a known manner to obtain analogs of compound XV in which the cyclic portion thereof is replaced with X in formula (1) above. Compounds XV having a chiral center can be further resolved to the chiral components with the use of a chiral resolving agent such as tartaric acid to give either enantiomers of the substituted compounds XV.

Scheme 7

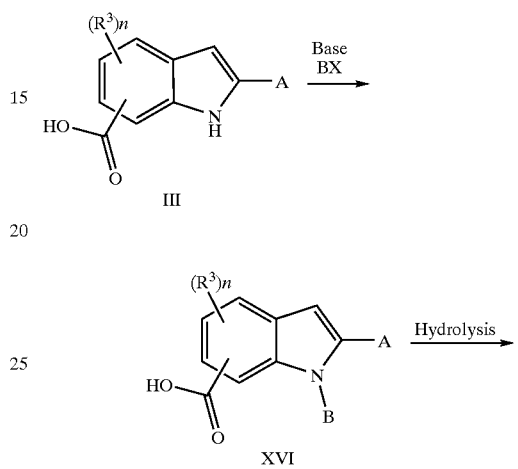

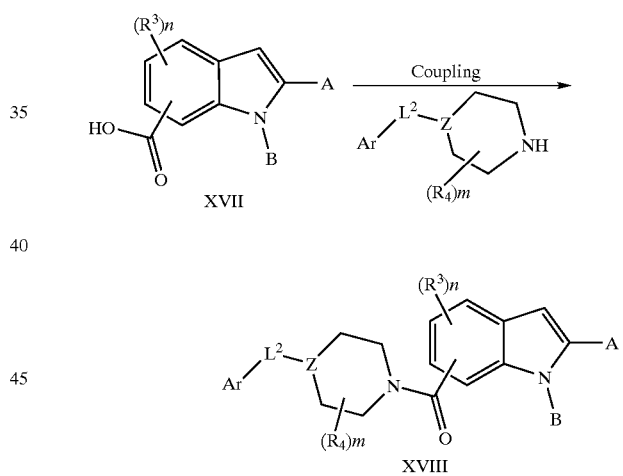

Compounds III can be treated with halides, acid chlorides and other electrophiles (BX), Scheme 7, containing a variety of different substituents, in the presence of a base such as sodium hydride, in a variety of different solvents, to give compounds of type XVI. These can then be converted to the corresponding acids XVII by treatment with appropriate reagents such as an aqueous base. As disclosed in commonly assigned U.S. Ser. No. 09/575,060, the acids may then be coupled to substituted amines IX, XII or XV using a coupling agent such as EDAC.HCl in a variety of solvents including methylene chloride, dimethyl formamide, to give compounds XVIII. In accordance with the present invention the piperazine/piperadine component of compound XVIII may be replaced with a cyclic aliphatic moiety "X" as defined in formula (1) above.

Scheme 8

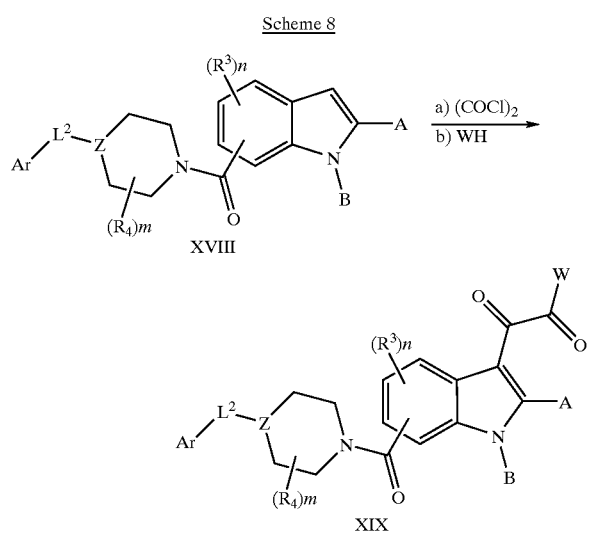

Compounds XVIII, or the analog thereof in which the piperazine/piperazine ring is replaced with "X" in formula (1) above can be first treated with acid chlorides such as oxalyl chloride in methylene chloride under anhydrous conditions followed by treatment with a variety of nucleophiles WH to give compounds of type XIX, Scheme 8.

Assays for p38 α Kinase Inhibition

For each of the assay procedures described below, the TNF-α production correlates to the activity of p38-α kinase.

A. Human Whole Blood Assay for p38 Kinase Inhibition

Venous blood is collected from healthy male volunteers into a heparinized syringe and is used within 2 hours of collection. Test compounds are dissolved in 100% DMSO and 1 μl aliquots of drug concentrations ranging from 0 to 1 mM are dispensed into quadruplicate wells of a 24-well microtitre plate (Nunclon Delta SI, Applied Scientific, So. San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37° C. Whole blood is cultured either undiluted or at a final dilution of 1:10 with RPMI 1640 (Gibco 31800+ $NaHCO_3$, Life Technologies, Rockville, Md. and Scios, Inc., Sunnyvale, Calif.). At the end of the incubation period, 10 μl of LPS (*E. coli* 0111:B4, Sigma Chemical Co., St. Louis, Mo.) is added to each well to a final concentration of 1 or 0.1 μg/ml for undiluted or 1:10 diluted whole blood, respectively. The incubation is continued for an additional 2 hours. The reaction is stopped by placing the microtitre plates in an ice bath and plasma or cell-free supernates are collected by centrifugation at 3000 rpm for 10 minutes at 4° C. The plasma-samples are stored at −80° C. until assayed for TNF-α levels by ELISA, following the directions supplied by Quantikine Human TNF-α assay kit (R&D Systems, Minneapolis, Minn.).

$IC_{50}$ values are calculated using the concentration of inhibitor that causes a 50% decrease as compared to a control.

B. Enriched Mononuclear Cell Assay for p38 Kinase Inhibition

The enriched mononuclear cell assay, the protocol of which is set forth below, begins with cryopreserved Human Peripheral Blood Mononuclear Cells (HPBMCs) (Clonetics Corp.) that are rinsed and resuspended in a warn mixture of cell growth media. The resuspended cells are then counted and seeded at 1×10⁶ cells/well in a 24-well microtitre plate. The plates are then placed in an incubator for an hour to allow the cells to settle in each well.

After the cells have settled, the media is aspirated and new media containing 100 ng/ml of the cytokine stimulatory factor Lipopolysaccharide (LPS) and a test chemical compound is added to each well of the microtitre plate. Thus, each well contains HPBMCs, LPS and a test chemical compound. The cells are then incubated for 2 hours, and the amount of the cytokine Tumor Necrosis Factor Alpha (TNF-α) is measured using an Enzyme Linked hnuunoassay (ELISA). One such ELISA for detecting the levels of TNF-α is commercially available from R&D Systems. The amount of TNF-α production by the HPBMCs in each well is then compared to a control well to determine whether the chemical compound acts as an inhibitor of cytokine production.

LPS Induced Cytokine Synthesis in HPBMCs
Cryopreserved HPBMC (cat#CC-2702 Clonetics Corp)
LGM-3 media (cat#CC-3212 Clonetics Corp)
LPS stock 10 μg/ml (Cat. No. L 2630 serotype 0111:B4 Sigma)
Human TNF-α ELISA (R&D Systems)
DNase I (10 mg/ml stock)
Preparation of Cells.
LGM-3 media warmed to 37° C.
5 μl of DNase I stock added to 10 ml media.
Cells thawed rapidly and dispersed into above.
Centrifuge 200×g×10 min @ RT.
Pellet up in 10 ml sterile PBS.
Centrifuge 200×g×10 min @ RT.
Pellet resuspended in 10 ml LGM-3 then diluted to 50 ml with LGM-3.
Perform cell count.
Adjust to 1×E06 cells/well.
Seed 1 ml/well of a 24 well plate.
Place plate in incubator to plate down for 1 hour.
Preparation of Incubation Media.
LGM-3 containing 100 ng/ml LPS (e.g. 50 ml media plus 0.5 ml LPS stock)
Aliquot into 2 ml aliquots and add 1000× inhibitor dilutions.
Incubation
When cells have plated down aspirate media away and overlay with 1 ml relevant incubation media. Return plate to incubator for 2 hours or 24 hours. Remove supernatants after incubation to a labeled tube and either perform TNF (or other) ELISA immediately or freeze for later assay.

$IC_{50}$ values are calculated using the concentration of inhibitor that causes a 50% decrease as compared to a control.

Administration and Use

The compounds of the invention are useful among other indications in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as Alzheimer's, coronary artery disease, congestive heart failure, cardiomyopathy, myocarditis, vasculitis, restenosis, such as occurs following coronary angioplasty, atherosclerosis, IBD, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, Gram-negative sepsis, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38-α, p38-β, p38-γ and p38-δ. Jiang, Y., et al., *J Biol Chem* (1996) 271:17920–17926 reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms.

Kumar, S., et al., *Biochem Biophys Res Comm* (1997) 235:533–538 and Stein, B., et al., *J Biol Chem* (1997) 272:19509–19517 reported a second isoform of p38-β, p38-β2, containing 364 amino acids with 73% identity to p38-α. All of these reports show evidence that p38-β is activated by proinflammatory cytokines and environmental stress, although the second reported p38-β isoform, p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α, thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z., et al., *Biochem Biophys Res Comm* (1996) 228:334–340 and of p38-δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38-α and either the putative p38-β1 or p38-β2 or both were reported by Jiang, Kumar, and Stein cited above as well as by Eyers, P. A., et al., *Chem and Biol* (1995) 5:321–328. An additional paper by Wang, Y., et al., *J Biol Chem* (1998)273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38-β activity results in hypertrophy, whereas activation of p38-α activity leads to myocyte apoptosis. Thus, selective inhibition of p38-α activity as compared to p38-β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

Thus, the invention encompasses the use of compounds which selectively inhibit the activity of the p38-α isoform for treating conditions associated with activation of p38-α, in particular those associated with cardiac hypertrophy, ischemia or other environmental stress such as oxidation injury, hyperosmolarity or other agents or factors that activate p38-α kinase, or cardiac failure, for example, congestive heart failure, cardiomyopathy and myocarditis.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

It should be noted that the compounds of formula (1) can be administered as individual active ingredients, or as mixtures of several embodiments of this formula. In addition, the inhibitors of p38 kinase can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implied above, although the compounds of the invention may be used in humans, they are also available for veterinary use in treating animal subjects.

The following examples are intended to illustrate but not to limit the invention. The compounds prepared below are inhibitors of p38.

EXAMPLE 1

6-Chloro-3-dimethylaminooxalyl-1-methyl-1H-indole-5-carboxylic acid (1-benzyl-pyrrolidin-3S-ylmethyl)-amide

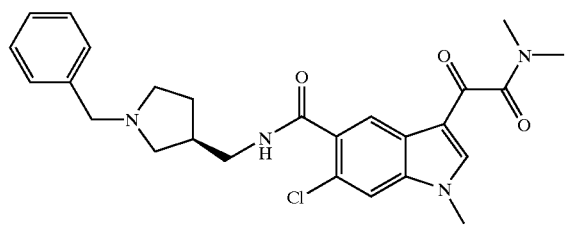

The above compound was prepared using the following reaction scheme:

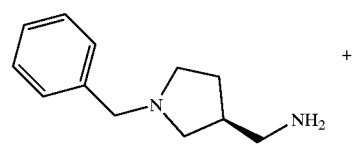

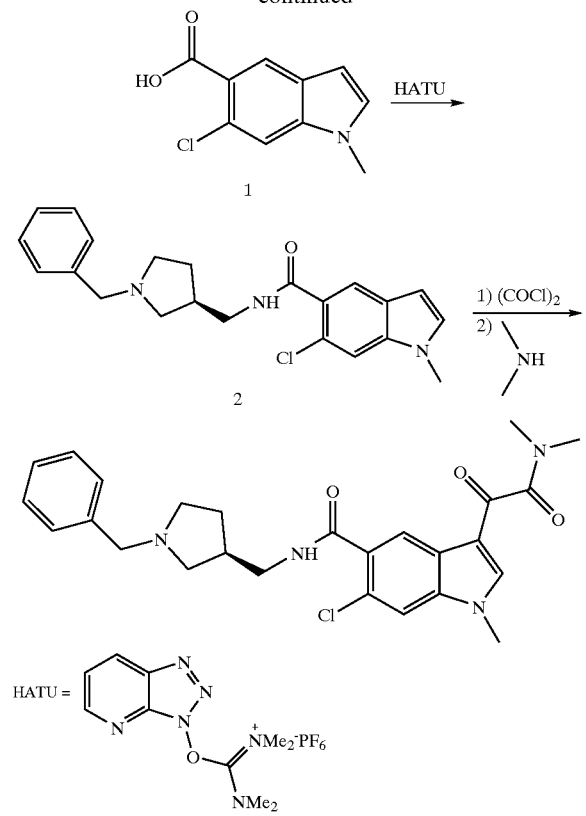

Step A

Synthesis of 2. To a solution of indole acid 1 (75 mg, 0.358 mMol) in DMF (1.5 mL) was added HATU (143 mg, 0.376 mMol) and triethylamine (92 mg, 0.716 mMol). After shaking occasionally for 15 min, this solution was added to (3R)-1-benzyl-3-(aminomethyl)pyrrolidine (82 mg, 0.430 mMol) and stirred overnight. The reaction was diluted with ethyl acetate and washed with water (×2) and brine. The organic layer was dried (Na$_2$SO$_4$), concentrated and chromatographed via radial chromatography (1:1 ETOAc:hexanes) to give 117 mg of a white solid.

Step B

Synthesis of Example 1 compound. A solution of Indole 2 (117 mg, 0.306 mMol) in DCM (4 mL) was cooled to 0° C. and a 2.0 M solution of oxalyl chloride (0.31 mL) in DCM was added dropwise via syringe. The reaction was stirred at 0° C. for one hour and then allowed to warm to room temperature for one hour. The solvent was removed under vacuum. The solvent was replaced by DCM (4 mL) cooled to 0° C. and a 2.0 M solution of dimethyl amine (0.62 mL) in DCM was added via syringe. After 0.5 h the solution was warmed to room temperature and stirred for an additional 30 minutes. The solvent was removed and the yellow residue re-suspended in DCM. The solution was washed with water, brine, dried (Na$_2$SO$_4$) and concentrated to give a yellow oil which was purified via radial chromatography (3:97 methanol:chloroform) to give 47 mg of a white solid.

EXAMPLE 2

6-Chloro-3-dimethylaminooxalyl-1-methyl-1H-indole-5-carboxylic acid (1-benzyl-pyrrolidin-3R-ylmethyl)-amide

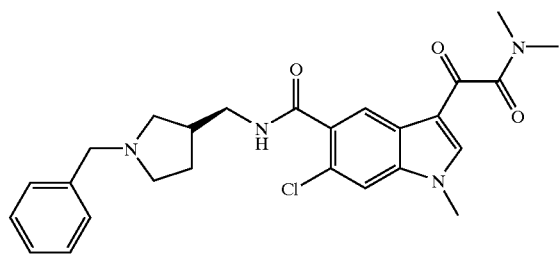

The above compound was prepared using the same procedure used in Example 1 using (3S)-1-benzyl-3-(aminomethyl)pyrrolidine in place of (3R)-1-benzyl-3-(aminomethyl)pyrrolidine.

EXAMPLE 3

2-{6-Chloro-5-[1-(4-fluoro-benzyl)-1,7-diaza-spiro[4.4]nonane-7-carbonyl]-1-methyl-1H-indol-3-yl}-N,N-dimethyl-2-oxo-acetamide

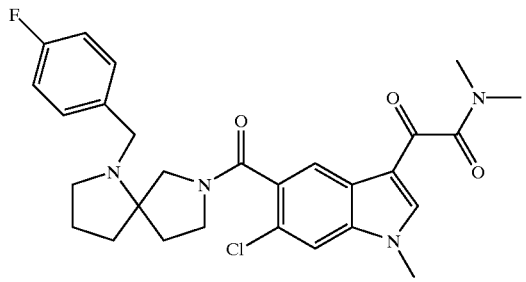

Step A

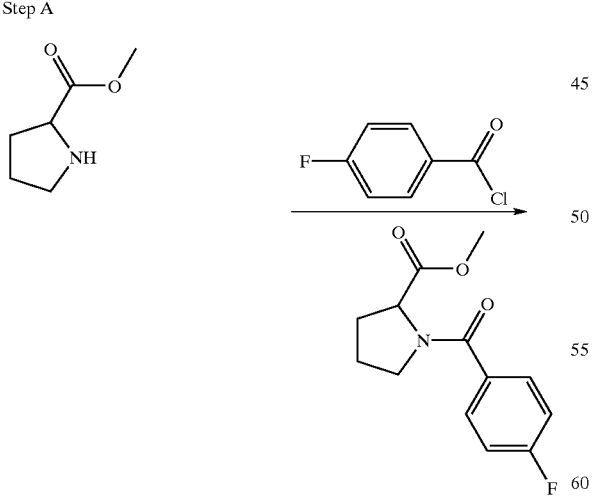

Triethylamine (7.88 g, 77.9 mMol) was added to a stirred solution of proline methyl ester (5.93 g, 35.4 mMol) in DCM (70 mL). The mixture was cooled to 0° C. and 4-fluorobenzoyl chloride (6.18 g, 39.0 mMol) was added slowly via syringe. The mixture was stirred for an additional 2 hr at 0° C. and allowed to warm to room temperature for an additional 2 h. The solution was then transferred to a separatory funnel, washed with 10% citric acid, 5% potassium carbonate, brine, dried (Na$_2$SO$_4$) and concentrated to give a thick oil. The residue was purified by flash chromatography to give 5.90 g of the product as a colorless oil.

Step B

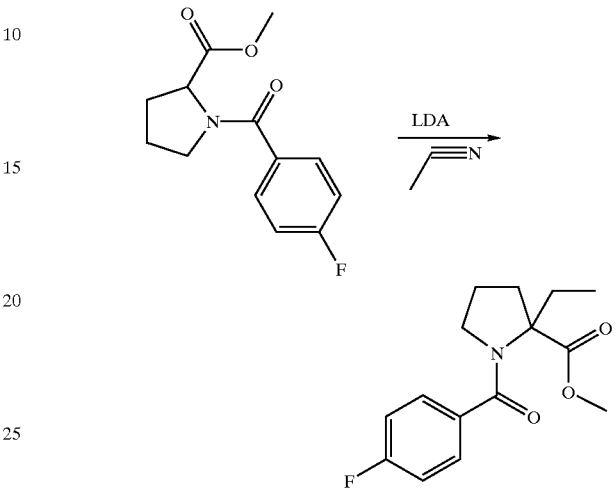

Tetraethylenediamine (3.09 g, 26.6 mMol) was added to a solution of lithium diisopropyl amide (2.61 g, 24.4 mMol) in THF (25 mL) at −78° C. After the solution was allowed to stir for 15 min, a solution of 1-chloroacetonitrile (2.51 g, 33.3 mL) in THF (6 mL) was added dropwise via addition funnel. The reaction was stirred for an additional 1 h at −78° C., warmed to 0° C. and stirred for an additional 30 min. The reaction was then concentrated for form a dark oil, partitioned between DCM-water and the solid was removed by filtration. The organic layer was separated, washed with 2.0 M HCl, brine, dried (Na$_2$SO$_4$) and concentrated to give a dark oil. The residue was chromatographed using flash chromatography (30:70 EtOAc:hexanes) to give 3.34 g of the desired product as a thick colorless oil.

Step C

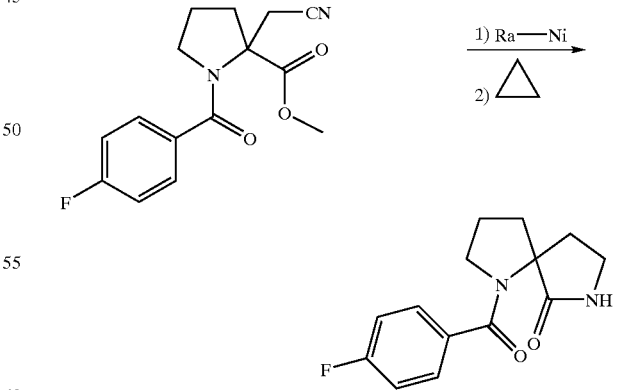

A solution of the nitrile (1.70 g, 5.82 mMol) was taken up in EtOH (50 mL). Using a 2 mL scoop, two scoops of Raney nickel in water was added. The reaction was placed on a Parr shaker at 45 PSI H$_2$ for 5 days with additional scoops of Raney nickel added on day 2 and 3. After 5 days LCMS indicated near complete reduction of the nitrile to primary amine. The solution was filtered through celite and concentrated to give slightly yellow oil. The oil was taken up in toluene (25 mL) and refluxed for 48 hours. After removing the solvent, the resulting oil was chromatographed via radial chromatography to give 640 mg of the product as a white solid. Material was used without further purification.

Step D

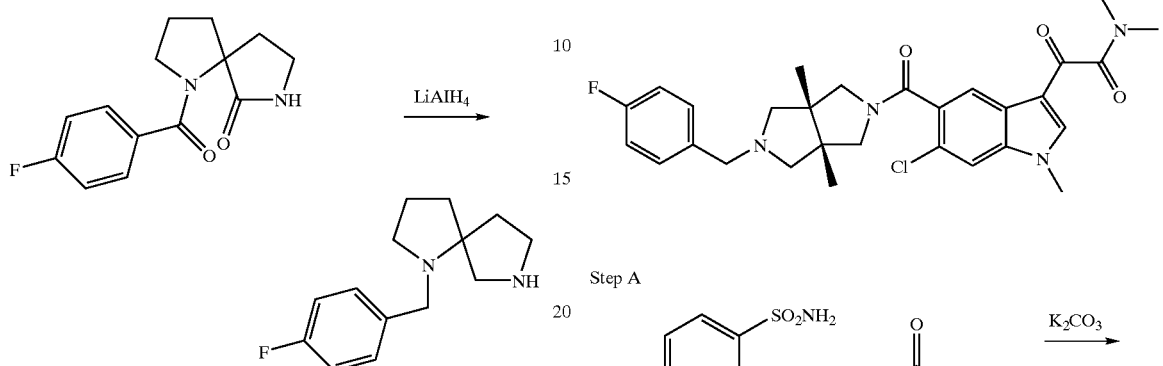

A solution of lithium aluminum hydride (2.3 mL, 2.29 mMol) in ether was added to a solution of the diamide in THF (20 mL). The reaction was heated to reflux overnight. An additional 2.3 mL of lithium aluminum hydride solution was added and again the reaction was allowed to reflux overnight. At this point solid lithium aluminum hydride (174 mg, 2.58 mMol) was added and the reaction was refluxed for an addition 4 hours. The reaction was cooled to 0° C. and 0.35 mL water was added. When the bubbling died down 0.35 mL 15% sodium hydroxide was added followed by 1.05 mL water and 5 g Na$_2$SO$_4$. The mixture was stirred for 1 h, filtered through celite and the solvent was removed to give a yellow oil that contains the crude product which was used without further purification.

Step E

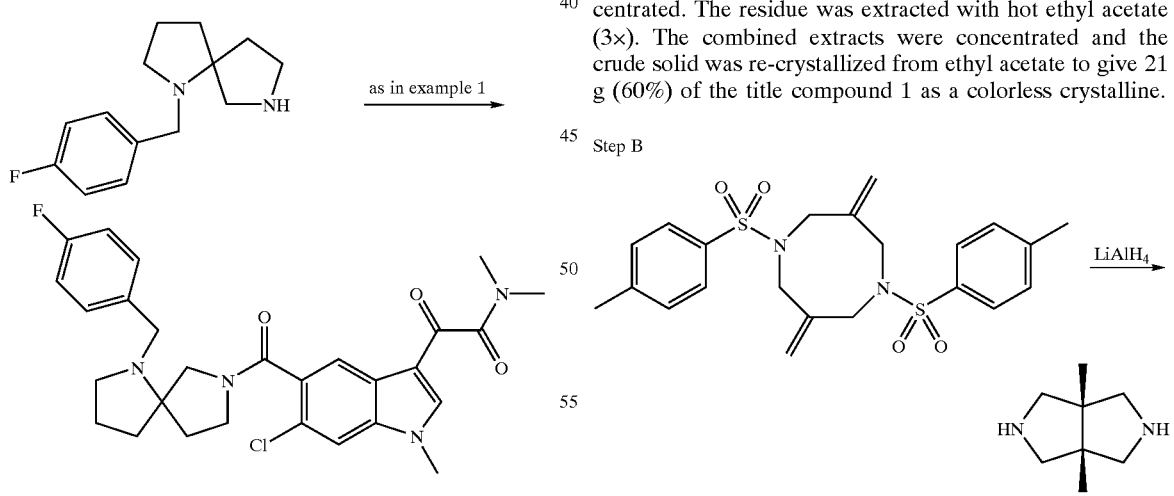

Synthesis of 2-{6-Chloro-5-[1-(4-fluoro-benzyl)-1,7-diaza-spiro[4.4]nonane-7-carbonyl]-1-methyl-1H-indol-3-yl}-N,N-dimethyl-2-oxo-acetamide was accomplished as described above for 6-Chloro-3-dimethylaminooxalyl-1-methyl-1H-indole-5-carboxylic acid (1-benzyl-pyrrolidin-3S-ylmethyl)-amide using 1-(4-Fluoro-benzyl)-1,7-diaza-spiro[4.4]nonane in place of (3R)-1-benzyl-3-(aminomethyl)pyrrolidine.

EXAMPLE 4

2-{6-Chloro-5-[5-(4-fluoro-benzyl)-3a,6a-dimethyl-hexahydro-pyrrolo[3,4-c]pyrrole-2-carbonyl]-1-methyl-1H-indol-3-yl}-N,N-dimethyl-2-oxo-acetamide

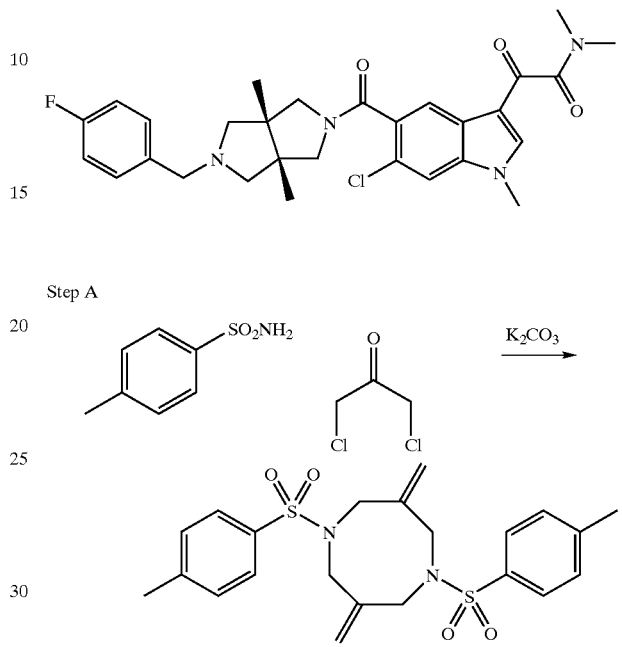

Step A

To a suspension of p-toluenesulfonamide (27.5 g, 1660 mMol) and anhydrous K$_2$CO$_3$ (45 g) in anhydrous acetonitrile (250 ml) was added 3-chloro-2-(chloromethyl)-1-propene (20 g, 160 mMol) in acetonitrile (25 mL) dropwise. The reaction mixture was refluxed for 4 h, and then concentrated. The residue was extracted with hot ethyl acetate (3×). The combined extracts were concentrated and the crude solid was re-crystallized from ethyl acetate to give 21 g (60%) of the title compound 1 as a colorless crystalline.

Step B

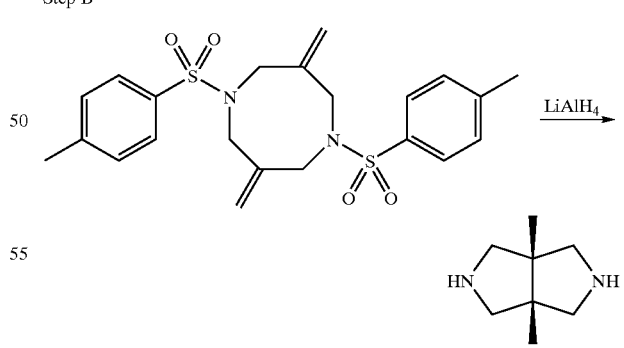

A slurry of N,N'-bis(p-toluenesulfonyl)-3,7-bis(methylene)-1,5-diazaacyclooctane (6.6 g, 9.9 mMol), LiAlH$_4$ (5.7 g, 150 mMol) in THF (200 mL) was stirred under N$_2$ for 2 days. The reaction mixture was quenched with 20% NaOH (15 mL) with external cooling and stirred continuously for 3 h. The precipitate was filtered off and washed with anhydrous ether. The combined extracts were concentrated to give 1.1 g of crude product containing some unidentified by-product. This product was used in the next reaction without further purification.

Step C

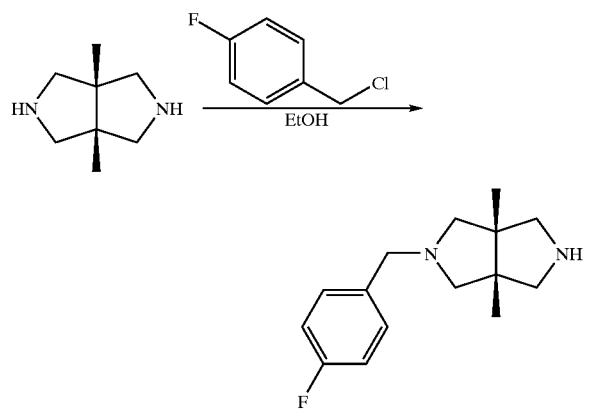

A mixture of the crude diamine (570 mg), 4-fluorobenzyl chloride (145 mg, 1 mMol) in EtOH was heated at reflux for 3 h. The reaction mixture was concentrated with $Na_2CO_3$ and extracted with EtOAc. The residue was purified by chromatography on silica gel eluting with 5% MeOH in $CH_2Cl_2$. (MeOH was increase to 100% gradually) to give 75 mg of the product as a white solid.

Step D

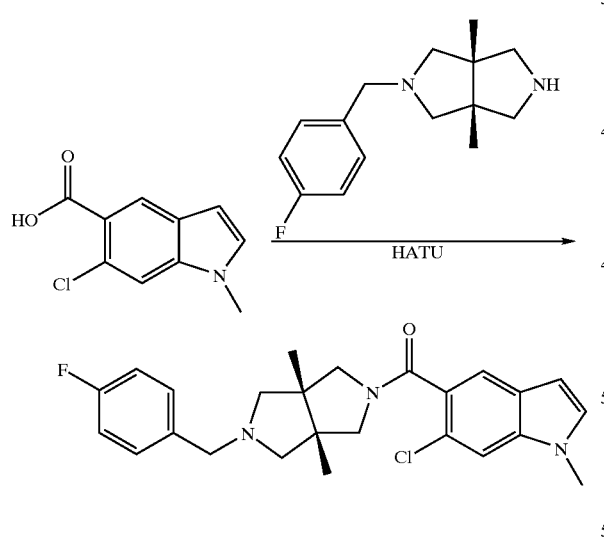

To a solution of indole (95 mg, 0.45 mMol) and amine 3 (75 mg, 0.3 mMol) in DMF was added HATU (172 mg, 0.45 mMol), followed by diisopropylethylamine (78 mg, 0.6 mMol). The reaction mixture was stirred at RT overnight, then concentrated. The residue was treated with $Na_2CO_3$, and extracted with EtOAc. The organic extracts was dried and concentrated. The residue was purified by chromatography on silica gel eluting with hexane:EtOAc (3:2) to give 50 mg (38%) of compound 6 as a white solid.

Step E

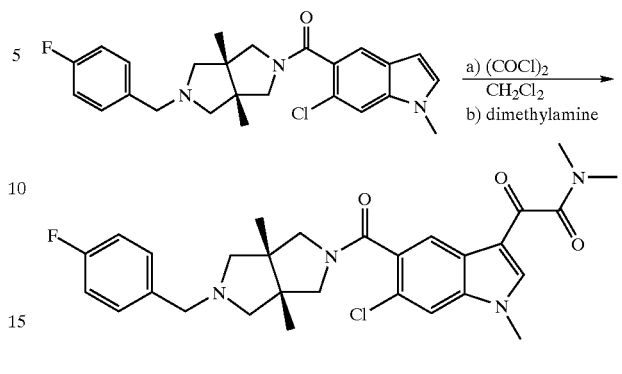

Oxalyl chloride (0.1 mL, 0.2 mMol) was added to a solution of indole in $CH_2Cl_2$ (5 mL) at 0° C. The reaction mixture was warmed to rt. slowly, stirred for 5 h, concentrated and then dried for 2 h. The residue was redissolved in $CH_2Cl_2$ and quenched with dimethylamine (0.2 mL, 0.4 mMol, 2 M in THF). The reaction mixture was treated with $Na_2CO_3$ and extracted with EtOAc. The combined extracts was dried and concentrated. The residue was purified on preparative TLC plate developed with 1% MeOH in EtOAc to give 2 mg of the desired product and 35 mg of the recovered starting material.

EXAMPLE 5

6-Chloro-3-dimethylaminooxalyl-1H-indole-5-carboxylic acid {2-[(4-fluoro-benzyl)-methyl-amino]-cyclohexyl}-amide Step A

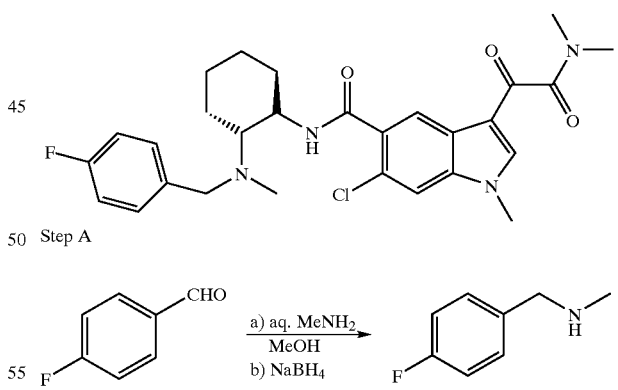

To 4-fluorobenzaldehyde (2.48 g) in MeOH was added methylamine (40% aqueous solution, 2.0 mL). The reaction mixture was stirred at RT for 12 h at which time $NaBH_4$ (0.38 g) was added. After stirring for 1 h the reaction was quenched with $H_2O$ and extracted with ethyl acetate. The combined extracts were dried, filtered, and concentrated to yield (4-fluorobenzyl)-methylamine (2.30 g) which was used without further purification.

Step B

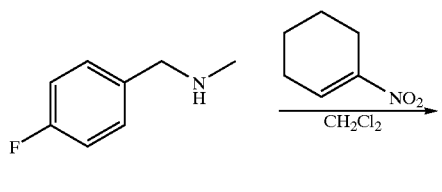

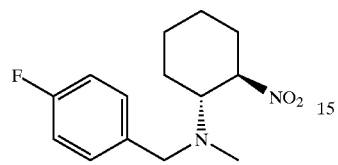

(4-Fluoro-benzyl)-methyl-(2-nitro-cyclohexyl)-amine was prepared by dissolving (4-fluorobenzyl)-methylamine (139 mg) in $CH_2Cl_2$ (2.25 mL) and treating it with 1-nitro-1-cyclohexane (127 mg) at −78° C. and slowly warming it to RT. After the reaction was complete as monitored by HPLC, the reaction mixture was concentrated to yield the desired product which was immediately in the next step.

Step C

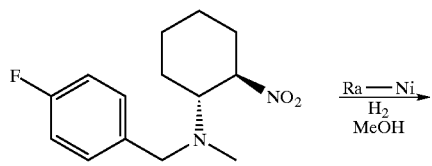

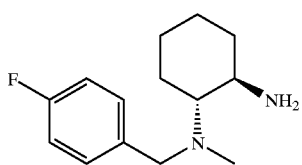

To crude (4-fluoro-benzyl)-methyl-(2-nitro-cyclohexyl)-amine (1.0 mMol) in (5:1) $MeOH/H_2O$ (30 mL) was added Raney-Nickel. The reaction mixture was placed under $H_2$ (1 atm) and stirred for 16 h. The slurry was filtered through Celite and the volatiles removed in vacuo to yield N-(4-Fluoro-benzyl)-N-methyl-cyclohexane-1,2-diamine (20 mg).

Step D

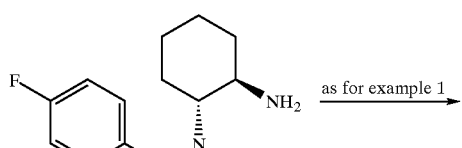

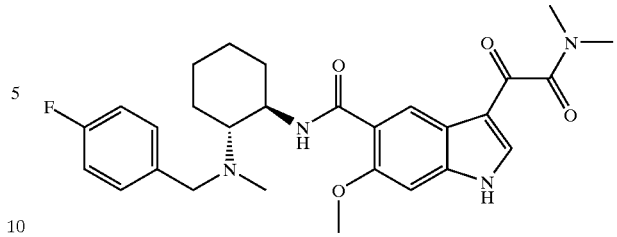

6-Chloro-3-dimethylaminooxalyl-1H-indole-5-carboxylic acid {2-[(4-fluoro-benzyl)-methyl-amino]-cyclohexyl}-amide was prepared as for Example 1.

EXAMPLE 6

2-{5-[1-(4-Fluoro-benzyl)-piperidine-4-carbonyl]-6-methoxy-1-methyl-1H-indol-3-yl}-N,N-dimethyl-2-oxo-acetamide

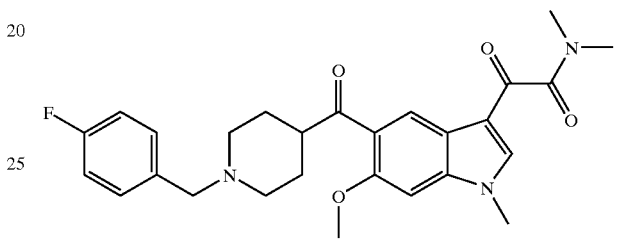

Step A

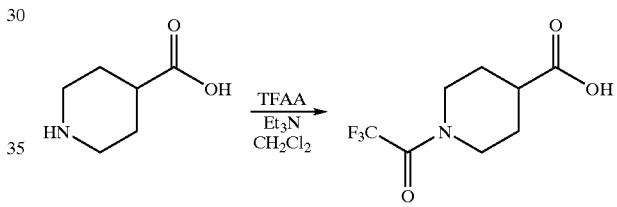

Isonipecotic acid (5.37 g, 44.2 mMol) was dissolved at −10° C. in $CH_2Cl_2$ under an atmosphere of argon. $Et_3N$ (6.53 ml, 46.4 mMol) was slowly added, followed by trifluoroacetic anhydride (6.62 ml, 46.4 mMol). The reaction mixture was stirred for 1 h at room temperature and then poured into $H_2O$. The organic phase was separated and evaporated to dryness. The crude material thus obtained was dissolved in $Et_2O$ and extracted into a 10% $NaHCO_3$ solution. Acidification to pH 4 with concentrated HCl and extraction with $CH_2Cl_2$ yielded, after evaporation, a white solid. (6.27 g, 27.85 mMol, 63% yield).

Step B

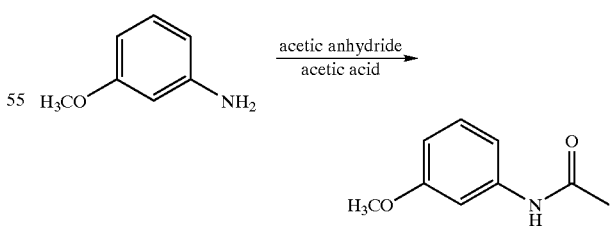

Acetic anhydride (10 ml) was added to a solution of m-anisidine (10 g) in 10 ml of acetic acid at 0° C. The solution was stirred overnight at room temperature and then poured into 50 g of ice and 50 ml of water. The light pink solid was filtered and air-dried, yielding 10.5 g of the product.

Step C

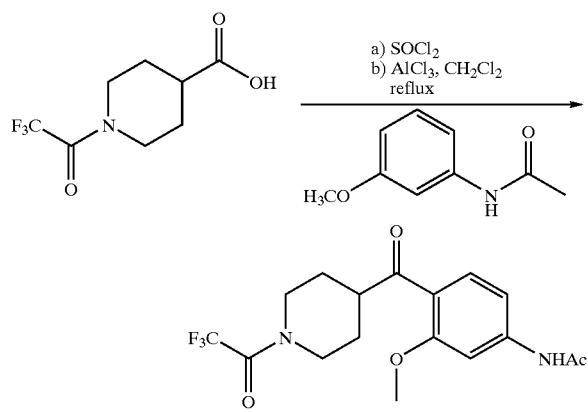

1.69 g (7.52 mMol) of amide was treated with 10 ml thionyl chloride at 0° C. followed by heating the reaction mixture at reflux temperature overnight. At the end of reaction, excess thionyl chloride was removed under reduced pressure to give 1.83 g of the acid chloride. 1.37 g of 3-methoxy-acetanilide (8.3 mMol) in 20 ml of dry $CH_2Cl_2$ was then added to the above acid chloride, followed by slowly addition of 2.51 g (18.8 mMol) aluminum chloride at ambient temperature. The reaction mixture was heated to reflux for 12 h. It was then cooled and poured into a mixture of conc. HCl and ice. Product was extracted with EtOAc and the organic layer was washed with water, half saturated sodium bicarbonate solution and concentrated. Silica gel column separation ($CH_2Cl_2$) gave 0.42 g (1.13 mMol) of the product.

Step D

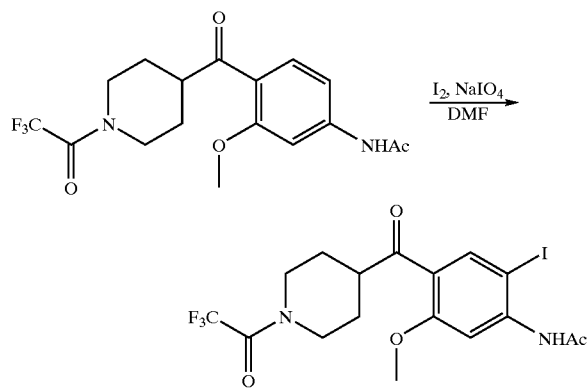

0.417 g of N-{3-Methoxy-4-[1-(2,2,2-trifluoro-acetyl)-piperidine-4-carbonyl]-phenyl}-acetamide (1.12 mMol) was dissolved in 5 ml of dry DMF followed by addition of 0.12 g sodium periodate (0.56 mMol), 0.284 g iodine (1.12 mMol). Under argon protection, the reaction mixture was warmed up to 50° C. with an oil bath and continued for 24 hours. DMF was removed in vacuo, residue was taken up in EtOAc and washed with $H_2O$, brine, dried over anhydrous sodium sulfate and concentrated. Silica gel column separation (20% EtOAc in Hexane) afforded 0.33 g of product.

Step E

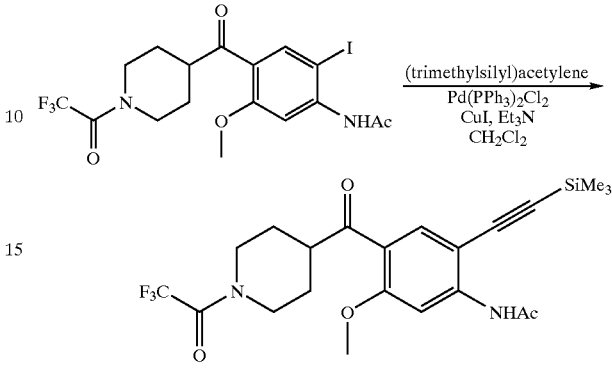

To a dry and $N_2$ filled 25 ml RB flask is added 0.5 g of N-{2-Iodo-5-methoxy-4-[1-(2,2,2-trifluoro-acetyl)-piperidine-4-carbonyl]-phenyl}-acetamide (1 mMol), 5 ml dry $CH_2Cl_2$, and 5 ml dry $Et_3N$. At 0° C., 0.11 ml trimethylsilylacetylene (1.1 mMol) is added dropwise. At the end of addition, the reaction mixture is warmed up to room temperature and stirred for 2 h. Solvent is evaporated off, residue which is then dissolved in EtOAc filtered through Celite. The combined filtrate is washed with brine, dried over anhydrous sodium sulfate and concentrated. Silica gel column separation (40% EtOAc in Hexane) provide 0.42 g of product.

Step F

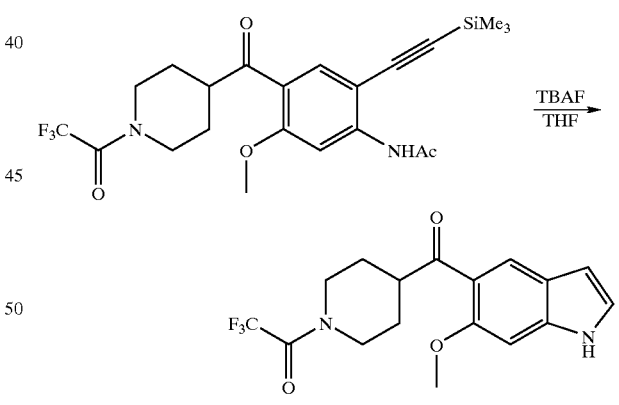

0.42 g of N-{5-Methoxy-4-[1-(2,2,2-trifluoro-acetyl)-piperidine-4-carbonyl]-2-trimethylsilanyl-ethynyl-phenyl}-acetamide (0.9 mMol) is dissolved in 5 ml dry THF. Under nitrogen protection, 1.8 ml tetrabutylammnonium fluoride (1.8 mMol, 1M in THF) is added. The mixture is then heated under reflux temperature for 1 h. After THF is removed, residue is dried under vacuum, re-dissolved in EtOAc, washed with $H_2O$, brine, dried over anhydrous sodium sulfate, and concentrated. Silical gel column separation (20% EtOAc in hexane) affords 0.22 g product.

Step G

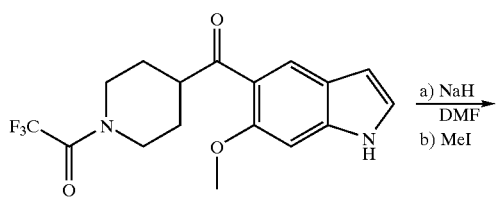

Under nitrogen protection, 177 mg of 2,2,2-Trifluoro-1-[4-(6-methoxy-1H-indole-5-carbonyl)-piperidin-1-yl]-ethanone (0.5 mMol) is dissolved in 10 ml dry DMF. To this solution is added 22 mg of NaH (0.55 mMol, 60% dispersion in mineral oil) at 0° C. After stirring at 0° C. for about 10 min, the reaction mixture is warmed up to room temperature with continued stirring for 0.5 h. The reaction mixture is cooled back to 0° C., followed by addition of 0.034 mL of methyl iodide (0.55 mMol). The reaction is allowed to stir at 0° C. for 0.5 h before being warmed up to room temperature and with continued stirring at room temperature for 1 h. DMF is removed under reduced pressure, residue is taken up in $CH_2Cl_2$, washed with $H_2O$, brine, dried over anhydrous sodium sulfate and concentrated. Silica gel column separation ($CH_2Cl_2$) affords 177 mg of product.

Step H

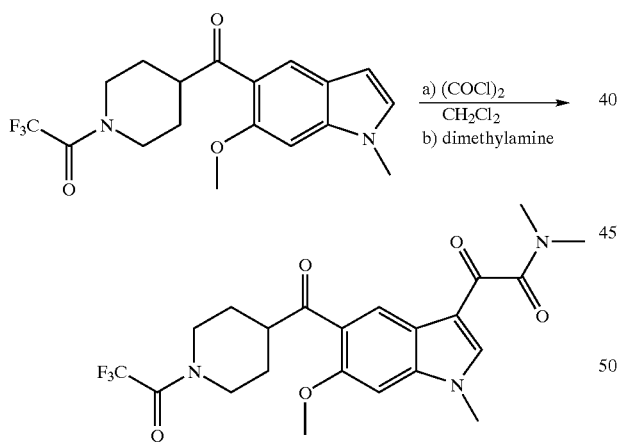

Under argon protection, 0.36 ml oxalyl chloride (0.72 mMol, 2M in $CH_2Cl_2$) is added into a 15-ml dry RB flask containing 177 mg of 2,2,2-Trifluoro-1-[4-(6-methoxy-1-methyl-1H-indole-5-carbonyl)-piperidin-1-yl]-ethanone (0.48 mMol) in 2 ml dry $CH_2Cl_2$ at 0° C. The reaction mixture is stirred at 0° C. for 10 min before being warmed up to room temperature and stirred at room temperature for 1 hour. Excess of oxalyl chloride is removed under vacuo and vacuum dried for 0.5 h. At 0° C., residue is dissolved in 2 ml dry $CH_2Cl_2$, followed by addition of 0.48 mL of dimethylamine (0.96 mMol, 2 M in THF). The reaction mixture is then stirred at 0° C. for 0.5 h before being warmed up to room temperature and stirring continued for 1 h. At the end of reaction, solvent is removed as well as unreacted dimethylamine residue. Residue is re-dissolved in $CH_2Cl_2$, washed with $H_2O$, brine, dried over anhydrous sodium sulfate and concentrated. Silica gel column separation (2% MeOH in $CHCl_3$) gave 204 mg of product.

Step I

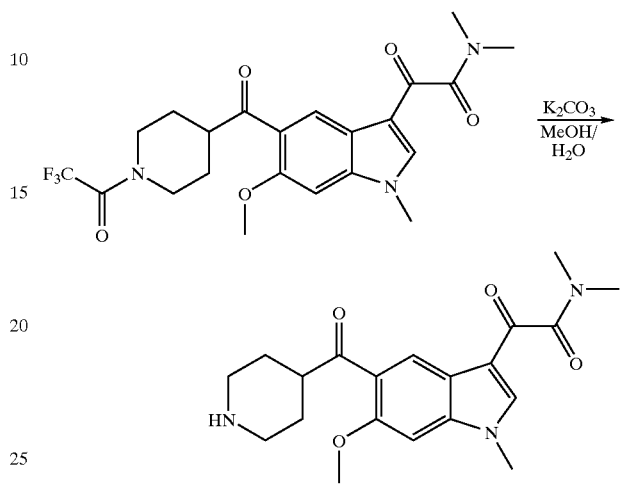

To a 4 ml MeOH solution of 204 mg of 2-{6-Methoxy-1-methyl-5-[1-(2,2,2-trifluoro-acetyl)-piperidine-4-carbonyl]-1H-indol-3-yl}-N,N-dimethyl-2-oxo-acetamide (0.44 mMol) is added 123 mg of KOH (2.2 mMol) in 4 ml $H_2O$. The reaction mixture is heated at reflux temperature for 1 h before being cooled down to room temperature. MeOH is removed in vacuo and 6 mL $H_2O$ is introduced to dilute the solution. Aqueous solution was then extracted with $CH_2Cl_2$ and organic layer is washed with brine, dried over anhydrous sodium sulfate and concentrated to give 145 mg of product.

Step J

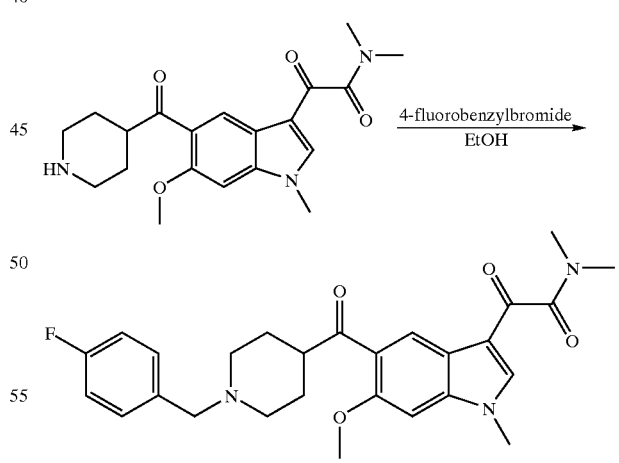

144 mg of 2-[6-Methoxy-1-methyl-5-(piperidine-4-carbonyl)-1H-indol-3-yl]-N,N-dimethyl-2-oxo-acetamide (0.39 mMol) is dissolved in 10 ml EtOH followed by the addition of 0.05 ml of 4-fluorobenzyl bromide (0.4 mMol). The reaction mixture is stirred at room temperature over night. After removing the solvent, residue is taken up in $CH_2Cl_2$ and washed with $H_2O$, brine, dried over anhydrous sodium sulfate and concentrated. Silica gel column separation (2% MeOH in $CH_2Cl_2$) then gives 133 mg of product.

ADDITIONAL EXAMPLES

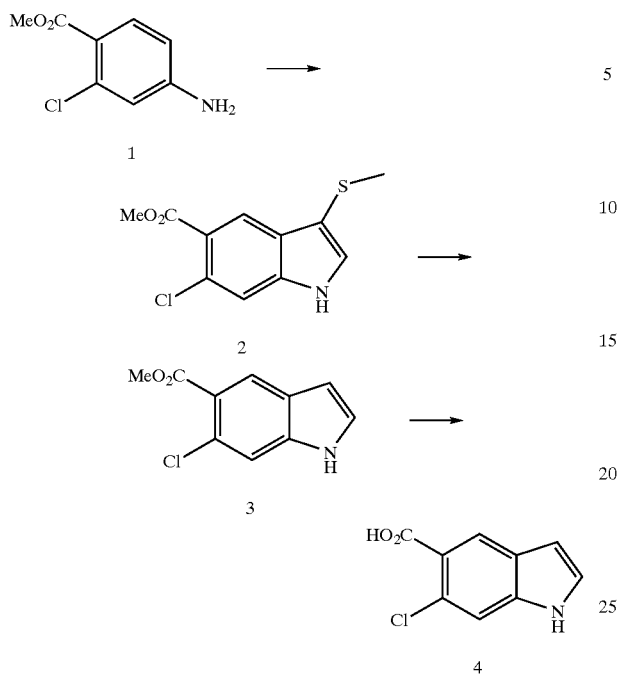

Synthesis of 2: Methyl 4-amino-2-chlorobenzoate (1) (18.5 g) was dissolved in dichloromethane (350 ml) and methyl thioacetaldehyde dimethylacetal (13.6 g) was added. The mixture was cooled to −45° C. (dry ice/acetonitrile bath). N-chlorosuccinamide (16.0 g) in 350 ml dichloromethane was added dropwise over 1 hr 30 min while maintaining bath temp at −45° C. The reaction mixture was stirred additional 1 hr, then triethylamine (16 mL, 100 mMols) in 30 ml dichloromethane was added dropwise over 5 min, reaction was warmed to room temp, then refluxed for 16 h. Solvent was removed and residue taken up in 500 ml carbon tetrachloride, triethylamine-hydrochloric acid was removed by filtration, filtrate was heated to reflux for 2 h. Solvent was removed by rotary evaporation.

The residue was dissolved in 250 ml tetrahydrofuran and 250 ml 10% hydrochloric acid was added. The mixture was stirred overnight at room temperature until the complete disappearance of the starting material was observed. Solvent was removed under vacuum, acidic aqueous solution was extracted with ethyl acetate (3×125 ml). The combined ethyl acetate extracts were washed with 10% hydrochloric acid, water and dried over anhydrous sodium sulfate. Solvent was removed under vacuum. Crude product mixture was purified on a silica column eluting with ethyl acetate:hexanes (15:85) to give 6.4 g of the desired product 2.

Synthesis of 3: Methyl 6-Chloro-3-thiomethyl-5-indole carboxylate (5.2 g) was dissolved in 150 ml ethanol:tetrahydrofuran (9:3) and treated with Raney-Nickel. Reaction was monitored by mass spec at 30 min intervals, with subsequent addition of Raney-Nickel until reaction was complete. When reaction was complete reaction was carefully filtered through celite and the celite washed with methanol several times and filtrate evaporated. Residue was taken up in ethyl acetate, washed with water, dried over anhydrous sodium sulfate. The solvent was removed to give 3 (3.2 g).

Synthesis of 4: Methyl ester 1.5 g was dissolved in 30 ml methanol/water 50:50. The reaction mixture was heated at 50° C. for 2 h with 4 Mol. equivalent sodium hydroxide. The reaction mixture was cooled in ice-bath, acidified to pH 3 with 5M hydrochloric acid. Removed methanol by rotary evaporation and extracted with ethyl acetate. The extract was washed with saturated sodium chloride and dried over anhydrous sodium sulfate. Evaporation of the solvent gave the desired acid 4 (1.48 g).

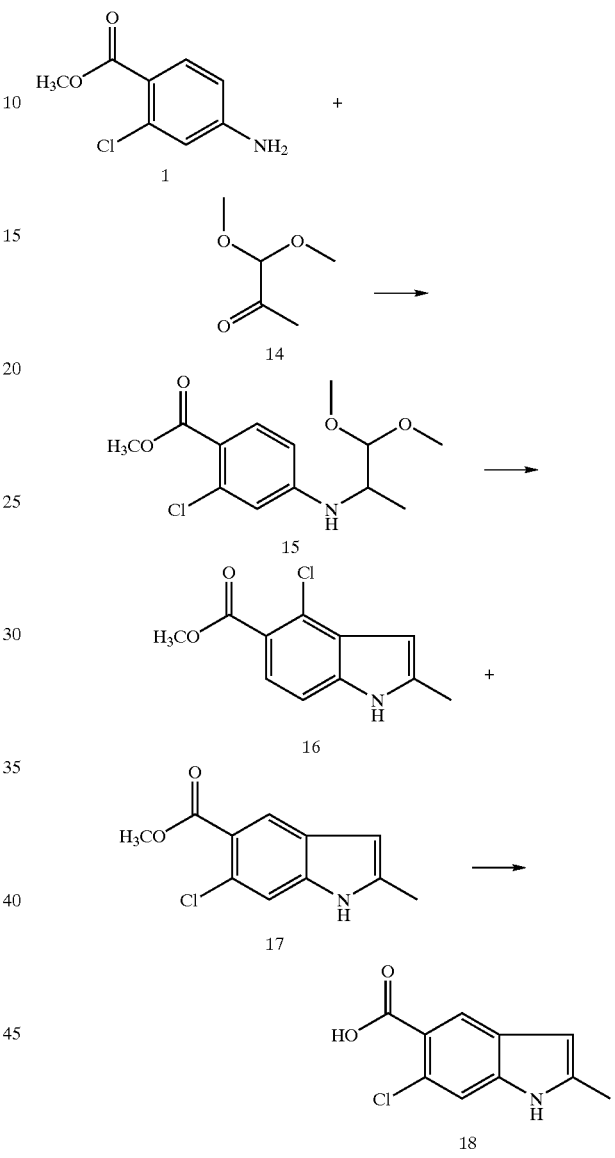

Synthesis of 15: To a solution of aniline 1 (9.25 g, 0.05 mol) and pyruvic aldehyde dimethyl acetal 14 (11.8 g, 0.1 mol) in 200 mL glacial acetic acid was added anhydrous sodium sulfate (71.0 g, 0.5 mol) and the mixture was stirred for 30 min. Powdered sodium triacetoxy borohydride (31.8 g, 0.15 mol) was then added in portions for a period of 5 min. The reaction mixture was stirred for an additional 2 h. Acetic acid was removed under reduced pressure and the residue was made basic by adding sufficient amount of saturated sodium bicarbonate solution. The product was then extracted with ethyl acetate, dried with sodium sulfate and evaporated to get an oil. This was chromatographed on silica gel column using ethyl acetate:hexane (3:7) to give 15 (14 g) as colorless oil.

Synthesis of 16 and 17: To a suspension of fresh aluminum chloride (18.5 g) in 200 ml dry chloroform at 0° C. was added a solution of ketal 15 (13.3 g) in 100 ml chloroform slowly and the mixture was allowed to warm up to the room temperature and stirred overnight. Ice-cold water was added carefully to quench the aluminum chloride and the organic layer was separated and washed with sodium bicarbonate solution, dried and evaporated to get a white solid. The isomers were separated using silica gel column chromatography using ethyl acetate:hexane (1:9). The 6-cholo indole 17 (2.0 g) eluted first followed by 4-chloro isomer 16 (3.8 g).

Synthesis of 18. To a solution of 1.3 g of indole 17 in 15 mL of methanol was added a solution of 0.9 g of sodium hydroxide in 20 mL of water. The reaction mixture was heated at 50° C. for 4 h where upon a clear solution resulted. Cooled and evaporated off methanol and the residue was diluted with water and acidified with 10% hydrochloric acid. The product was extracted with ethyl acetate. The organic layer was dried over sodium sulfate, filtered and evaporated to obtain indole acid 18 (1.2 g) as white solid.

2-Methyl-6-methoxyindole-5-carboxylic acid was also synthesized using the above synthetic procedure.

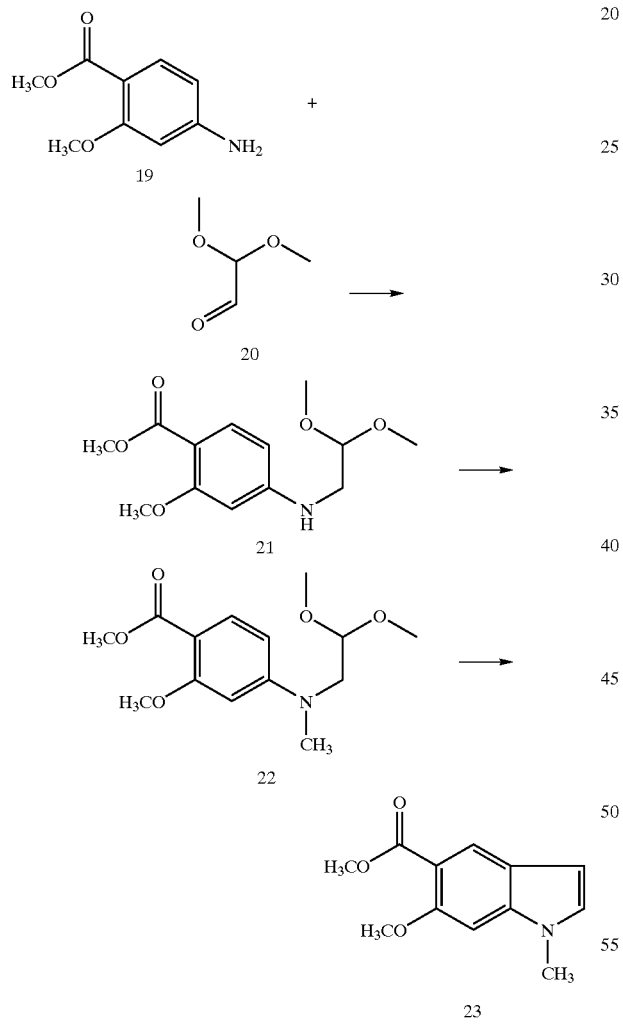

Synthesis of 21: To a solution of methyl 4-amino-6-methoxy 5-benzoate (19) (6.0 g, 0.033 mol) and dimethyl acetal 20 (7.0 g, 0.066 mol) in 150 mL glacial acetic acid was added anhydrous sodium sulfate (47.0 g, 0.33 mol) and the mixture was stirred for 30 min. Powdered sodium triacetoxy borohydride (20.1 g, 0.099 mol) was then added in portions for a period of 5 min. The reaction mixture was stirred for an additional 2 h. Acetic acid was removed under reduced pressure and the residue was made basic by adding sufficient amount of saturated sodium bicarbonate solution. The product was then extracted with ethyl acetate, washed with saturated sodium chloride, dried over sodium sulfate and evaporated to get an oil. This was chromatographed on silica gel column using ethyl acetate:hexane (3:7) as eluent and the desired product 21 was obtained (5.2 g) as an oil.

Synthesis of 22: To a solution of 21 (3.6 g) and iodomethane (5.7 g) in 50 mL anhydrous dimethylformamide was added potassium t-butoxide (1.0 M in tetrahydrofuran, 20 mL) at ambient temperature. The reaction mixture was stirred at ambient temperature for 0.5 h and poured into 250 mL ethyl acetate, washed with water (4×100 mL), brine (50 mL) and dried over magnesium sulfate. Evaporation of solvent afforded 3.26 g of 22. The product was used for next step without purification.

Synthesis of 23: To a suspension of anhydrous aluminum chloride (0.71 g) in 20 mL anhydrous 1,2-dichloroethane was added, dropwise a solution of 22 (1 g) in 10 mL 1,2-dichloroethane with stirring. The reaction was heated to 80° C. for 0.5 h. At the end of this time, the reaction mixture was quenched with methanol, solvents evaporated, then ethyl acetate (100 mL) was added. The organic phase was washed with water, aq. sodium bicarbonate and brine and concentrated. The crude product was purified by silica chromatography using ethyl acetate:hexane (3:7) to give 23 0.22 g.

What is claimed is:

1. A compound of the formula:

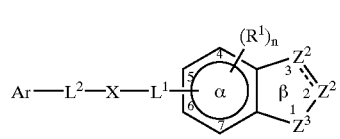

and the pharmaceutically acceptable salts thereof wherein:

Ar is an aryl group substituted with 0–5 substituents selected from the group consisting of alkyl, alkenyl, alkynyl, aryl, arylalkyl, acyl, aroyl, heteroaryl, NH-aroyl, halo, OR, $NR_2$, SR, SOR, $SO_2R$, OCOR, NRCOR, $NRCONR_2$, NRCOOR, $OCONR_2$, RCO, COOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl and wherein two of said optional substituents on adjacent positions can be joined to form a fused, optionally substituted aromatic or nonaromatic, saturated or unsaturated ring which contains 3–8 members;

$L^2$-X-$L^1$ is of the formula:

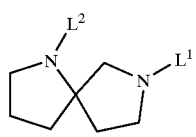

$L^1$ is CO, $SO_2$ or alkylene (1-4C);

$L^2$ is alkylene (1-4C) or alkenylene (2-4C) optionally substituted with one or two moieties selected from the group consisting of alkyl, alkenyl, alkynyl, aryl, arylalkyl, acyl, aroyl, heteroaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, and $R_3Si$, wherein each R is independently H, alkyl, alkenyl or aryl and wherein two substituents on $L^2$ can be joined to form a non-aromatic saturated or unsaturated ring that includes 0–3 heteroatoms which are O, S and/or N and which contains 3 to 8 members or said two substituents can be joined to form a carbonyl moiety or an oxime, oximeether, oximeester or ketal of said carbonyl moiety;

n is 0–3;

each $R^1$ is independently halo, alkyl, OCOR, OR, NRCOR, SR, or NR2, wherein R is hydrogen, alkyl, or aryl;

represents a single or double bond;

one $Z^2$ is CA or $CR^2A$; the other $Z^2$ is $CR^3$, $CR^3_2$, $NR^4$ or N; and each $R^2$, $R^3$ and $R^4$ are independently selected from the group consisting of H, alkyl, alkenyl, alkynyl, aryl, arylalkyl, acyl, aroyl, heteroaryl, NH-aroyl, halo, OR, $NR_2$, SR, SOR, $SO_2R$, OCOR, NRCOR, $NRCONR_2$, NRCOOR, $OCONR_2$, RCO, COOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl and two of $R^2$ and/or $R^3$ on adjacent positions can be joined to form a fused, optionally substituted aromatic or nonaromatic, saturated or unsaturated ring which contains 3–8 members, or an oxime, oximeether, oximeester or ketal thereof;

$Z^3$ is $NR^5$ or O; where $R^5$ is H or is optionally substituted alkyl, alkenyl, alkynyl, aryl, arylalkyl, acyl, aroyl, heteroaryl, or is SOR, $SO_2R$, RCO, COOR, alkyl-COR, $SO_3R$, $CONR_2$, $SO_2NR_2$, CN, $CF_3$, $NR_2$, OR, alkyl-SR, alkyl-SOR, alkyl-$SO_2R$, alkyl-OCOR, alkyl-COOR, alkyl-CN, alkyl-$CONR_2$, or $R_3Si$, wherein each R is independently H, alkyl, alkenyl or aryl;

A is —$W_i$—$COX_jY$, where Y is selected from $COR^6$, tetrazole, 1,2,3-triazole, 1,2,4-triazole, and imidazole, each of W and X is substituted or unsubstituted alkylene or alkenylene, each of 2–6 Å; each of i and j is independently 0 or 1; and $R^6$ is H, or is straight or branched chain alkyl, alkenyl, alkynyl, aryl, arylalkyl, heteroaryl, or heteroarylalkyl, each optionally substituted with halo, alkyl, SR, SOR, $SO_2R$, $SO_2NR_2$, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl or aryl, or wherein $R^6$ is OR, $NR_2$, SR, $NRCONR_2$, $OCONR_2$, or $NRSO_2NR_2$, wherein each R is independently H, alkyl, alkenyl or aryl and wherein two R attached to the same atom may form a 3–8 member carbocyclic or heterocyclic ring and wherein said ring may further be substituted by alkyl, alkenyl, alkynyl, aryl, arylalkyl, heteroaryl, heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl or aryl wherein two R attached to the same atom may form a 3–8 member ring, optionally substituted as above defined.

2. The compound of claim 1 wherein Y is $COR^6$.

3. The compound of claim 2 wherein Y is tetrazole; 1,2,3-triazole; 1,2,4-triazole; or imidazole.

4. The compound of claim 1 wherein each of i and j is 0.

5. The compound of claim 1 wherein j is 0.

6. The compound of claim 1 wherein $Z^3$ is $NR^5$.

7. The compound of claim 1 wherein $R^5$ is H, or is optionally substituted alkyl or acyl.

8. The compound of claim 1 wherein $R^2$ and $R^3$ are independently selected from halo, OR and alkyl.

9. The compound of claim 1 wherein the compound is:

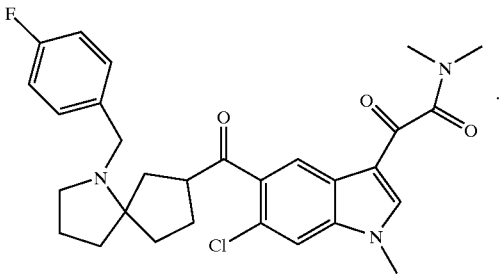

10. The compound of claim 1 wherein $L^1$ is $CH_2$ or CO and $L^2$ is $CH_2$ or CHOH.

11. The compound of claim 10 wherein $L^1$ is CO.

12. The compound of claim 1 wherein $L^2$ and/or $L^1$ is unsubstituted alkylene.

13. The compound of claim 1 wherein $L^2$ and/or $L^1$ is unsubstituted methylene, or methylene substituted with alkyl.

14. The compound of claim 1 wherein Ar is optionally substituted phenyl.

15. The compound of claim 14 wherein said optional substitution is by halo, OR, or alkyl.

16. The compound of claim 15 wherein said phenyl is unsubstituted or has a single substituent.

17. The compound of claim 1 wherein $R^1$ is halo or alkoxy.

18. The compound of claim 17 wherein n is 0, 1 or 2.

19. The compound of claim 1 wherein $L^1$ is coupled to the α ring at the 4-, 5- or 6-position.

20. The compound of claim 1 wherein $Z^2$ at position 3 is CA or CHA.

21. The compound of claim 20 wherein the $Z^2$ at position 2 is $CR^3$ or $CR^3_2$.

22. The compound of claim 21 wherein $R^3$ is hydrogen, or is selected from the group consisting of alkyl, alkenyl, alkynyl, aryl, arylalkyl, acyl, aroyl, heteroaryl, NH-aroyl, halo, OR, $NR_2$, SR, SOR, $SO_2R$, OCOR, NRCOR, $NRCONR_2$, NRCOOR, $OCONR_2$, RCO, COOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl and two of $R^1$ can be joined to form a fused, optionally substituted aromatic or nonaromatic, saturated or unsaturated ring which contains 3–8 members.

23. The compound of claim 22 wherein each $R^3$ is selected from the group consisting of H, alkyl, acyl, aryl, arylalkyl, heteroaryl, halo, OR, $NR_2$, SR, NRCOR, RCO, COOR, and CN, wherein each R is independently H, alkyl or aryl.

24. The compound of claim 20 wherein $Z^2$ at position 2 is N or $NR^4$.

25. The compound of claim 24 wherein $R^4$ is H, or alkyl, alkenyl, alkynyl, aryl, arylalkyl, acyl, aroyl, heteroaryl, or is SOR, $SO_2R$, RCO, COOR, alkyl-COR, $SO_3R$, $CONR_2$, $SO_2NR_2$, CN, $CF_3$, or $R_3Si$ wherein each R is independently H, alkyl, alkenyl or aryl.

26. The compound of claim 1 wherein

represents a double bond.

27. A pharmaceutical composition which composition comprises a therapeutically effective amount of a compound of claim 1 and a pharmaceutically acceptable excipient.

28. A method to treat rheumatoid arthritis, which comprises administering to a subject in need of such treatment a compound of claim 1 or a pharmaceutical composition thereof.

* * * * *